(12) United States Patent
Mahuran et al.

(10) Patent No.: US 7,488,721 B2
(45) Date of Patent: *Feb. 10, 2009

(54) REAL TIME METHYLUMBELLIFERONE-BASED ASSAY

(75) Inventors: Don Mahuran, Toronto (CA); Michael Tropak, Toronto (CA); Eric Brown, Oakville (CA)

(73) Assignees: McMaster University, Hamilton, Ontario (CA); Hospital for Sick Children, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/129,274

(22) Filed: May 13, 2005

(65) Prior Publication Data

US 2006/0008862 A1 Jan. 12, 2006

Related U.S. Application Data

(60) Provisional application No. 60/570,458, filed on May 13, 2004.

(51) Int. Cl.
*A61K 31/7068* (2006.01)
*H01L 21/8238* (2006.01)
(52) U.S. Cl. ......................... 514/49; 438/206
(58) Field of Classification Search ........................ None
See application file for complete search history.

(56) References Cited

U.S. PATENT DOCUMENTS 6,140,115 A * 10/2000 Kolodny et al. .......... 435/320.1
2002/0035072 A1* 3/2002 Fan et al. ....................... 514/25

FOREIGN PATENT DOCUMENTS

WO WO 2004/103368 12/2004

OTHER PUBLICATIONS

Kolodny et al. Human Leukocyte Acid Hydrolases: Characterization of Eleven Lysosomal Enzymes and Study of Reaction Conditions for Their Automated Analysis; Clinica Chimica Acta, vol. 70 (1976) pp. 247-257.*

Dienes et al. Characteristics of the 4-Methylumbelliferone Laser Dye; The Journal of Quantum Electronics; vol. QE-9, No. 8 (1973) pp. 833-843.*
Van den Hout et al. Long Term Intravenous Treatment of Pompe Disease With Recombinant Human Alpha-Glucosidase from Milk; Pediatrics, vol. 113, No. 5 (2004) pp. e448-e457.*
Broadhead et al. Alpha-Glucosidase in Pompe Disease; J. Inher. Met. Dis. vol. 1 (1978) pp. 153-154.*
Sels et al. Miglitol (Bay M 1099) Has No Extraintestinal Effects on Glucose Control in Healthy Volunteers; Brit. J. Clin. Pharm. vol. 42, No. 4 (1996) pp. 503-506.*
Gee et al. Fluorogenic Substrates Based on Fluorinated Umbelliferones for Continuous Assays of Phosphatases and Beta-Galactosidases; Analytical Biochemistry, vol. 273 (1999) pp. 41-48.*
Bieringer et al. Neuraminidase in Juvenile Calf Thymus: Determination and Characterization by a Continuous Fluorometric Assay Procedure; Thymus, vol. 15 (1990) pp. 233-240.*
Wraith J.E.. Advances in Thetreatment of Lysosomal Storage Disease; Developmental Medicine and Child Neurology, vol. 43 (2001) pp. 639-646.*
Bayleran et al., (1984) "Synthesis of 4-methylumbelliferyl-βD-N-acetylglucosamine-6-sulfate and its use in classification of $GM_2$ gangliosidosis genotypes", Clin. Chem. Acta, v. 143, pp. 73-89.
Tropak et al, (2004) "Pharmacological Enhancement of β-Hexosaminidase Activity in Fibroblasts from Adult Tay-Sachs and Sandhoff Patients", J. Biol Chem. v. 279, pp. 13478-13487.
Application Note SAFIRE (2001) TECAN, "Shifts in Emission and Excitation Spectra due to pH Changes", pp. 1 to 7.

* cited by examiner

*Primary Examiner*—Jon P Weber
*Assistant Examiner*—Paul C. Martin
(74) *Attorney, Agent, or Firm*—Myers Bigel Sibley & Sajovec, P.A.

(57) ABSTRACT

A method is provided for determining the activity of an enzyme which releases methylumbelliferone (MU) from an MU-containing substrate wherein the enzyme has a pH optimum below the pKa of MU comprising: contacting a sample suspected of containing the enzyme with the MU-containing substrate at a pH suitable for activity of the enzyme to allow release of MU by the enzyme; contacting the sample with light of a wavelength in the range of about 310 nm to about 350 nm; determining fluorescence produced by the released MU, thereby determining the activity of the enzyme. This real time method provides improved diagnostic methods, for example for diseases associated with an abnormal level of activity of a glycosidase. The real time assay also can be used to screen compounds for their ability to modulate enzyme activity using MU-containing substrates.

3 Claims, 19 Drawing Sheets

Probucol 4,4 Áå-Isopropylidinedithio-bis-(2,6-di-tert-butyl)phenol (PRIOR ART)

(PRIOR ART)

A

MAC-0002984

| Parameter | Value | Std. Error |
|---|---|---|
| Y Range | 306.8671 | 361.5571 |
| IC 50 | 65.4263 | 99.9196 |
| Slope factor | 1.8893 | 2.2060 |
| Background | 812.9675 | 357.5426 |

B

MAC-0019672

| Parameter | Value | Std. Error |
|---|---|---|
| Y Range | 866.1514 | 65.9091 |
| IC 50 | 12.8300 | 14.6065 |
| Slope factor | 4.5007 | 16.1991 |
| Background | 653.2885 | 56.1008 |

C

MAC-0022971

| Parameter | Value | Std. Error |
|---|---|---|
| Y Range | 2769.8397 | 2245.2564 |
| IC 50 | 1.7636 | 2.5533 |
| Slope factor | 0.3312 | 0.3082 |
| Background | -461.5542 | 944.7638 |

D

MAC-0026024

| Parameter | Value | Std. Error |
|---|---|---|
| Y Range | 708.3641 | 84.4999 |
| IC 50 | 30.7135 | 6.7009 |
| Slope factor | 7.4843 | 20.0040 |
| Background | 903.4092 | 74.5954 |

E MAC-0026463

| Parameter | Value | Std. Error |
|---|---|---|
| Y Range | 1962.4866 | 812.8761 |
| IC 50 | 270.2587 | 256.1775 |
| Slope factor | 0.7556 | 0.3087 |
| Background | -343.7836 | 807.5201 |

F MAC-0026553

| Parameter | Value | Std. Error |
|---|---|---|
| Y Range | 497.3317 | 98.0522 |
| IC 50 | 20.5535 | 7.2257 |
| Slope factor | 2.4342 | 1.3844 |
| Background | 1130.4484 | 87.5973 |

G MAC-0027352

| Parameter | Value | Std. Error |
|---|---|---|
| Y Range | 720.9525 | 548.7853 |
| IC 50 | 39.7160 | 52.2965 |
| Slope factor | 1.6176 | 1.3000 |
| Background | 828.6568 | 528.7624 |

H MAC-0027368

| Parameter | Value | Std. Error |
|---|---|---|
| Y Range | 891.5740 | 1018.4522 |
| IC 50 | 42.6270 | 91.9855 |
| Slope factor | 1.2952 | 1.4991 |
| Background | 663.5839 | 980.4932 |

I

MAC-0028322

| Parameter | Value | Std. Error |
|---|---|---|
| Y Range | 1735.3769 | 148.2998 |
| IC 50 | 28.8635 | 9.1330 |
| Slope factor | 2.1072 | 1.2894 |
| Background | 0.0000 | 0.0000 |

J

MAC-0028324

| Parameter | Value | Std. Error |
|---|---|---|
| Y Range | 3900.7592 | 1579.2897 |
| IC 50 | 179.9701 | 105.5532 |
| Slope factor | 1.0532 | 0.2370 |
| Background | -2568.7210 | 1571.0908 |

K

MAC-0028347

| Parameter | Value | Std. Error |
|---|---|---|
| Y Range | 3025.3193 | 629.2476 |
| IC 50 | 71.0343 | 25.4423 |
| Slope factor | 1.2354 | 0.1832 |
| Background | -1683.5097 | 619.0181 |

L

MAC-0000573

| Parameter | Value | Std. Error |
|---|---|---|
| Y Range | 19626.0894 | 28085.5038 |
| IC 50 | 384.6901 | 1279.8507 |
| Slope factor | 0.6741 | 0.2456 |
| Background | -18388.6363 | 27922.2005 |

M

MAC-0031516

| Parameter | Value | Std. Error |
|---|---|---|
| Y Range | 2453.2791 | 1258.2887 |
| IC 50 | 35.2234 | 35.1103 |
| Slope factor | 1.1531 | 0.7977 |
| Background | -1185.7406 | 1185.9601 |

N

MAC-0031526

| Parameter | Value | Std. Error |
|---|---|---|
| Y Range | 430.7362 | 43.3957 |
| IC 50 | 24.0221 | 4.0084 |
| Slope factor | 1.8701 | 0.4484 |
| Background | 874.8719 | 39.2868 |

O

MAC-0031860

| Parameter | Value | Std. Error |
|---|---|---|
| Y Range | 2228.9473 | 986.4665 |
| IC 50 | 138.1111 | 111.0234 |
| Slope factor | 0.9881 | 0.3572 |
| Background | -965.4489 | 977.9845 |

P

MAC-0031850

| Parameter | Value | Std. Error |
|---|---|---|
| Y Range | 1528.6303 | 246.1620 |
| IC 50 | 0.2016 | 0.1443 |
| Slope factor | 0.6834 | 0.1554 |
| Background | 32.2985 | 35.3616 |

Q

MAC-0031862

| Parameter | Value | Std. Error |
|---|---|---|
| Y Range | 2061.9277 | 515.8594 |
| IC 50 | 108.5295 | 53.6427 |
| Slope factor | 0.9484 | 0.1871 |
| Background | -761.3200 | 508.9269 |

R

MAC-0031867

| Parameter | Value | Std. Error |
|---|---|---|
| Y Range | 1895.0849 | 344.0147 |
| IC 50 | 30.5860 | 15.5692 |
| Slope factor | 0.6641 | 0.1184 |
| Background | -468.7217 | 311.7505 |

S

MAC-0032527

| Parameter | Value | Std. Error |
|---|---|---|
| Y Range | 672.1287 | 452.0493 |
| IC 50 | 41.5734 | 69.2621 |
| Slope factor | 1.0808 | 0.4911 |
| Background | 696.0145 | 437.2922 |

T

MAC-0034700

| Parameter | Value | Std. Error |
|---|---|---|
| Y Range | 2542.4035 | 472.0060 |
| IC 50 | 45.3708 | 11.9238 |
| Slope factor | 2.2431 | 0.5296 |
| Background | -1189.0700 | 460.3693 |

U

MAC-0000659

| Parameter | Value | Std. Error |
|---|---|---|
| Y Range | 1584.3379 | 428.9606 |
| IC 50 | 34.2954 | 21.5138 |
| Slope factor | 0.9093 | 0.2634 |
| Background | 113.2944 | 402.1223 |

V

MAC-0035014

| Parameter | Value | Std. Error |
|---|---|---|
| Y Range | 37339.9692 | 18357.2558 |
| IC 50 | 162.8233 | 94.2244 |
| Slope factor | 1.4162 | 0.2086 |
| Background | -35712.8561 | 18338.4470 |

W

MAC-0037955

| Parameter | Value | Std. Error |
|---|---|---|
| Y Range | 2099.6811 | 341.0063 |
| IC 50 | 71.6744 | 32.8426 |
| Slope factor | 0.6469 | 0.0920 |
| Background | -428.4539 | 325.5048 |

X

MAC-0045373

| Parameter | Value | Std. Error |
|---|---|---|
| Y Range | 5923.5433 | 209.6963 |
| IC 50 | 5.8776 | 0.4437 |
| Slope factor | 1.1083 | 0.0909 |
| Background | 381.2409 | 150.3533 |

US 7,488,721 B2

REAL TIME METHYLUMBELLIFERONE-BASED ASSAY

RELATED APPLICATION INFORMATION

This application claims the benefit of U.S. Provisional application No. 60/570,458, filed May 13, 2004, which is incorporated by reference herein in its entirety.

FIELD OF THE INVENTION

The invention relates to methods for determining enzyme activity and more particularly to a real time assay employing a methylumbelliferone-based substrate. The invention further relates to diagnostic methods employing the real time assay, to screening methods for identifying potential pharmaceutical compounds and to uses of potential pharmaceutical compounds so identified.

BACKGROUND OF THE INVENTION

Fluorogenic methylumbelliferone-based substrates have been used in a number of assays of enzyme activity. For example, many lysosomal exo-glycosidases associated with lysosomal storage diseases (LSDs) lack significant specificity for the aglycone residue of their substrates. This has enabled the measurement of the activity of these enzymes using a substrate consisting of the fluorophore, methylumbelliferone (MU), attached to the appropriate sugar molecule. MU-based enzyme assays have been widely used for the diagnosis of LSDs such as Tay Sachs Disease, Sandhoff Disease and Gaucher Disease, which are associated with deficient levels of activity of lysosomal enzymes.

For Tay Sachs Disease and Sandhoff Disease, 4-methyl-umbelliferyl-N-acetyl-βD-glycosaminide (MUG) and 4-methyl-umbelliferyl-βD-N-20acetylglucosamine-6-sulphate (MUGS) have been used as substrates to measure the total activity of hexosaminidases A, B and S and hexosaminidases A and S respectively (Bayleran et al., (1984), Clin. Chem. Acta, v. 143, p. 73). Like other lysosomal enzymes, the hexosaminidases have maximal activity at around pH 4.5 but the methylumbelliferone (MU) produced by cleavage of the substrate has a pKa of 7.8 and is poorly fluorescent at the acid pH of maximal enzyme activity, necessitating adjustment of the pH to a pH higher than the pKa, thereby terminating enzyme activity, to provide adequate fluorescence for a sensitive assay. This has meant that hexosaminidase assays using MU-based substrates were endpoint assays, not readily adaptable for high throughput screening.

It has been found that sub-inhibitory concentrations of competitive inhibitors of certain lysosomal enzymes can increase activity of the enzymes sufficiently to offer a means of treatment of a number of lysosomal storage diseases. This phenomenon has been demonstrated in Fabry disease, both in mice and humans, using inhibitors of α-galactosidase. Mutant Hexosaminidase A has also been shown to have improved activity in the presence of sub-inhibitory concentrations of inhibitors, offering a new therapeutic approach in Tay-Sachs disease and Sandhoff disease (Tropak et al. (2004), J. Biol. Chem. v. 279, pp.13478-13487; International Patent Application WO 2004/103368). A similar phenomenon has been noted for glucocerebrosidase, which is deficient in Gaucher disease.

There is therefore a need for an improved method of assaying the activity of lysosomal enzymes, both to assist in diagnosis and to allow high through-put screening of candidate compounds, so that potentially therapeutic inhibitors of these enzymes can be identified.

SUMMARY OF THE INVENTION

In one aspect, the invention provides a method for determining the activity of an enzyme which releases methylumbelliferone (MU) from an MU-containing substrate wherein the enzyme has a pH optimum below the pKa of MU comprising:

contacting a sample suspected of containing the enzyme with the MU-containing substrate at a pH suitable for activity of the enzyme to allow release of MU by the enzyme;

contacting the sample with light of a wavelength in the range of about 310 nm to about 350 nm;

determining the fluorescence produced by the released MU, thereby determining the activity of the enzyme.

MU has pKa of 7.8 and many enzymes of interest, for example lysosomal enzymes, have optimum pH's in the acidic range, below the pKa of MU. The method of the invention avoids the need to adjust the pH of the reaction mixture to permit sensitive detection of the fluorescence and permits real time analysis of the activity of such enzymes while maintaining the convenience and sensitivity provided by use of an MU-containing substrate.

In a further aspect, the invention provides improved diagnostic methods. A method is provided for diagnosing a disease associated with an abnormal level of activity of at least one glycosidase in a subject comprising determining the activity of the at least one glycosidase enzyme in a sample obtained from the subject by the method as described above, wherein a level of enzyme activity different from the level of activity in a control sample suggests that the subject suffers from the disease.

In a further aspect, the method described above facilitates a new high throughput screening method of candidate compounds for their effect on the activity of such enzymes. A method is provided for screening a candidate compound for its ability to modulate the activity of an enzyme which releases MU from an MU-containing substrate comprising determining the activity of the enzyme in the presence and absence of the compound by the method as described above, wherein determination of a different level of enzyme activity in the presence or absence of the compound indicates that the compound modulates the activity of the enzyme.

In a further aspect, the invention provides a number of compounds which show inhibitory activity against hexosaminidases, glucocerebrosidase and alpha-glucosidase and are therapeutic drug candidates for treatment of diseases wherein the activity of these enzymes is deficient. A method is provided for treating, in a subject, a disease associated with reduced activity of a lysosomal enzyme selected from the group consisting of hexosaminidase, glucocerebrosidase and alpha-glucosidase comprising administering to the subject an effective amount of a compound selected from the group consisting of pyrimethamine, dimethylsulfoxid, thioguanine and probucol for reduced activity of hexosaminidase, miglitol or castanospermine for reduced activity of glucocerebrosidase and miglitol for reduced activity of alpha-glucosidase.

DESCRIPTION OF THE INVENTION

Figure 1:
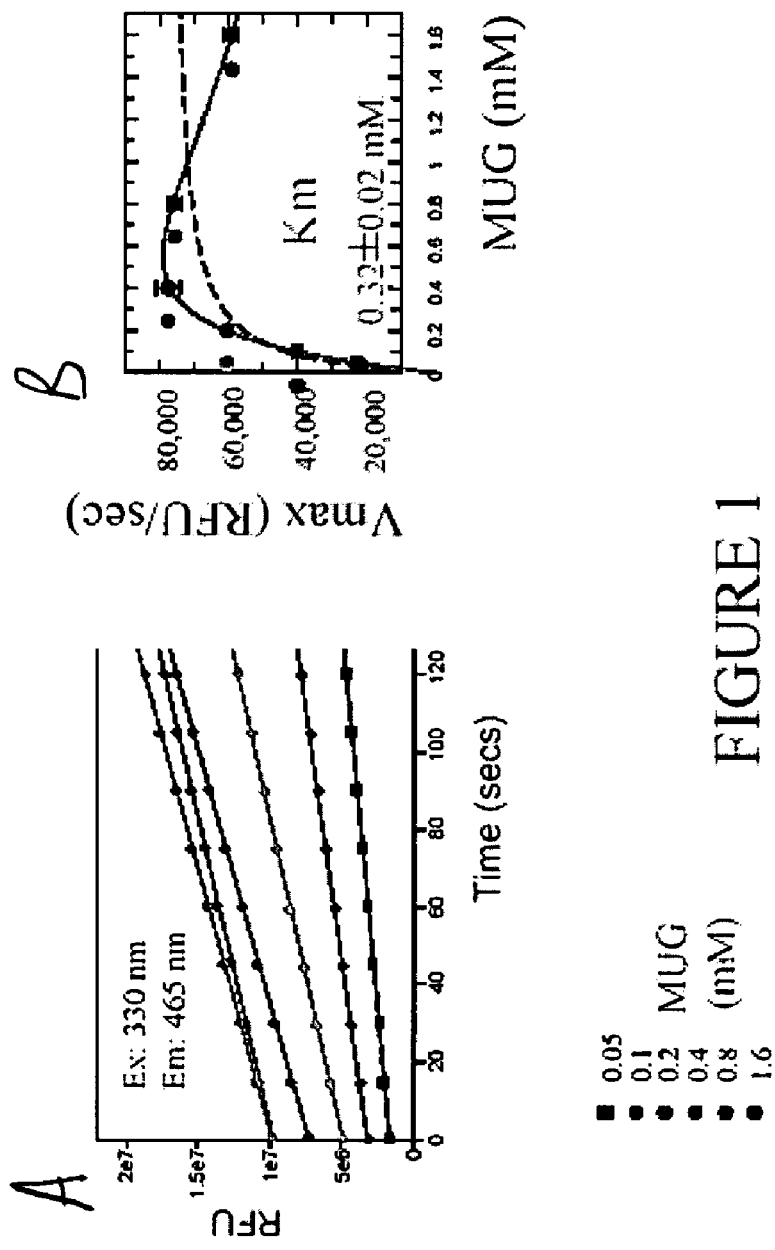
FIG. 1A shows human hexosaminidase A activity expressed as Relative Fluorescence Units (RFU) at various times in the presence of various concentrations of MUG.
FIG. 1B shows a dose response curve of human hexosaminidase A activity in the presence of various concentrations of MUG. Dashed line shows data fitted to classical Michaelis-Menton Kinetics and solid line shows data fitted to classical kinetics with substrate inhibition.
Figure 2:
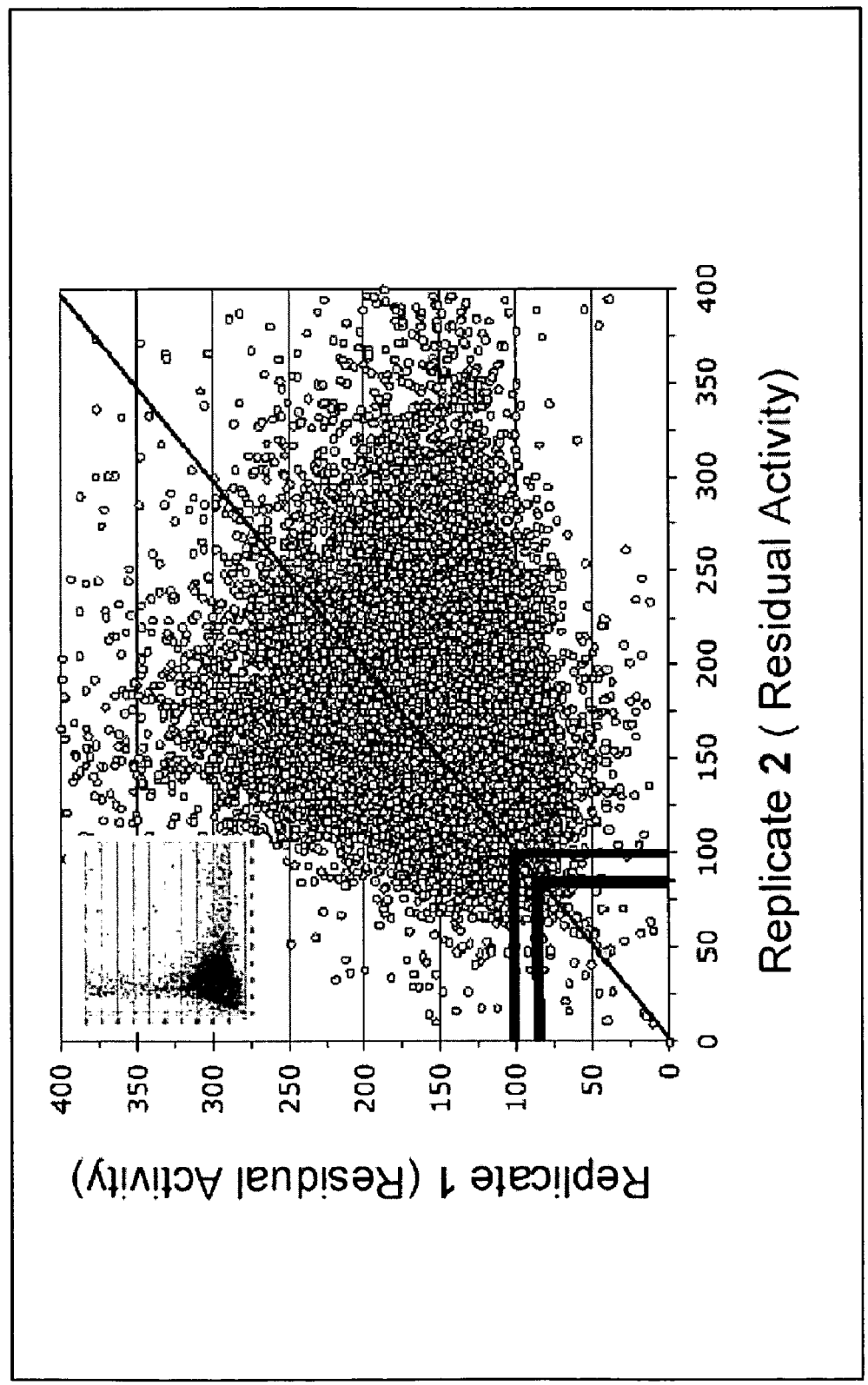
FIG. 2 shows graph of Replicate 1 against Replicate 2 residual hexosaminidase activity values from compound screen.

An "MU-containing substrate" is a compound in which an MU molecule is conjugated to a portion of an enzyme's normal substrate to form a compound which can still be hydrolysed by the enzyme, thereby releasing MU which can be detected and measured by its fluorescence.

MU-containing substrates have been important particularly in assaying lysosomal enzymes, which typically have acidic pH optima and can readily cleave the MU-glycoside corresponding to their natural substrate. As discussed above, such assays were end point assays, as the reaction mixture was adjusted to a basic pH, at or above the pKa of MU, for fluorescence measurement. This pH adjustment effectively terminated the enzyme reaction.

The present invention provides a real time, kinetic assay of enzyme activity using a methylumbelliferone-based substrate. By decreasing the wavelength of the exciting light from 365 nm to a wavelength in the range of about 310 nm to about 350 nm, for example about 320 to 340 nm, or for example 340 nm, it is possible to obtain adequate fluorescence at an acidic pH, since the excitation maximum of MU is blue-shifted with increasing acidity. When an excitation wavelength of 320 nm is used, the emission maximum at 450 nm is virtually identical at pH 5 and pH 10. This permits assays employing MU-containing substrates to be carried out in real time, thus facilitating high throughput screening by simplifying the procedure and reducing the occurrence of false negatives.

The method of the invention is applicable to any assay of enzyme activity using an MU-containing substrate where the pH optimum of the enzyme being assayed is below the pKa of MU. For enzymes which are glycosidases, the appropriate MU-glycoside is employed. Such enzymes include the enzymes of Table 1, which are related to the indicated disorders.

The method is also applicable to assays employing MU-conjugated peptides, lipids or other carbohydrate substrates for assaying peptidases, lipases etc. where the optimum pH of the enzyme is below the pKa of MU.

In one embodiment, the invention provides a method for assaying the activity of hexosaminidase A, B or S or cytosolic hexosaminidase (O-glcNase-O-glucosaminidase) using an MU-based substrate and detecting the fluorescence of the MU produced using an excitation wavelength in the range 310 nm to 350 nm and an emission wavelength in the range 440 nm to 480 nm, without pH adjustment of the reaction mixture. An excitation wavelength of 320 nm and an emission wavelength of 450 nm may be used.

Diagnostic tests for many lysosomal storage diseases are based on determining the activity of a relevant lysosomal enzyme in a tissue or bodily fluid of a subject, for example in serum or white blood cells. Such tests frequently employ a methylumbelliferone derivative of the relevant sugar as substrate in an end point assay. These tests may now be carried out in real time using the method of the invention, which permits automation of the method and greater efficiency in the diagnostic laboratory.

Such diagnostic tests may be used for patient and pre-natal diagnosis, for monitoring of treatment progress or for detection of disease carriers. All of the disorders listed in Table 1 are routinely diagnosed using a fluorometric assay based on MU; these diagnostic tests can be more conveniently handled and automated using the method of the invention.

The previously described end point assay methods, using MU-glycoside substrates, may be readily replaced by the real time assay of the invention, wherein without adjusting the pH of the reaction mixture away from the acidic pH for enzyme activity, an excitation wavelength in the range of about 310 nm to about 350 nm is employed for determination of released MU. Enzyme incubation conditions, such as pH, buffer and co-factors, for each enzyme are as previously described for end point assays. The examples herein also outline suitable incubation conditions for the described enzyme assays. Samples used for these diagnostic tests include blood, serum, tissue samples or cell lines grown from patient tissues.

For example, the real time assay described herein has been shown to be convenient for determining hexosaminidase activity in serum, fibroblast lysates and brain tissue, beta-galactosidase in Morquio disease fibroblast lysates, using MU-beta-galactoside, GCC in Gaucher disease fibroblast lysates using MU-beta-glucopyranoside, and alpha-glucosidase in Pompe disease fibroblast lysates using MU-alpha-glucopyranoside.

The method of the present invention also forms the basis of a high throughput screening method to screen candidate compounds for their ability to modulate the activity of a particular enzyme which can be assayed using an MU-containing substrate. For example, as discussed above, competitive inhibitors of various lysosomal enzymes have been found to stabilize the enzymes and to be useful therapeutically in lysosomal storage diseases. Candidate compounds can now be rapidly screened for their ability to inhibit such lysosomal enzymes, using the method of the invention, as described in the examples.

Previously available end point, MU-based assays were not suitable for rapid, high throughput screening of small molecule libraries to identify new candidate activity-enhancing compounds. The method of the invention has been shown to provide the basis for a rapid high throughput screening method which can identify candidate compounds. A primary screen of a 960-compound small molecule library and of a 46,000-compound small molecule library has been conducted, examining the inhibitory effect of the compounds on the activity of purified hexosaminidase A.

These screens yielded 10 and 64 initial hits respectively. These initial hit compounds were further examined at a range of concentrations in a secondary screen and 24 compounds which gave classical IC50 dose response curves were identified and their IC50s calculated. A number of compounds were identified which had IC50s in the low micromolar to high nanomolar range.

Some of these hit compounds have been examined in detail for their ability to enhance hexosaminidase activity; SP00124, PHG 00899, JFD 02087, Elinafide, 1,8 naphthalimide, and pyrimethamine, gave good enhancement of activity in adult Tay Sach Fibroblasts and Infantile Sandhoff fibroblasts.

The invention provides a method of treating a lysosomal storage disease, such as Tay Sachs, Sandhoff, San Fillipo, Fabry or Morquio Disease, comprising administering to a subject in need of such treatment an effective amount of one or more of the following compounds: SP00124, PHG 00899, JFD 02087, Elinafide, pyrimethamine, HH00659 and thioguanine. Miglitol, which is used to treat the adult onset form of diabetes, inhibits glucocerebrosidase and alpha-glucosidase and can be used to treat the late onset form of Gaucher and Pompe diseases.

The above compounds may also be used to treat diseases associated with a deficiency of an enzyme closely related to hexosaminidase, such as San Fillipo Disease (alpha-N-acetylglucosaminidase), alpha-N-acetyl galactosaminidase, alpha-galactosidase (Fabry disease) and beta galactosidase (Morquio Disease).

Hexosaminidase enhancers may be administered to a subject in need of treatment either alone or along with a pharmaceutically acceptable carrier; administration may, for example, be oral or parenteral, intravenous or subcutaneous. The enhancers may be formulated in liposomes for administration. Suitable methods of formulation are known to those of skill in the art and are described in texts such as Remington's Pharmaceutical Sciences (Mack Publishing Company, Easton, Pa., U.S.A. 1985). A serum level of enhancer compound in the range from 0.01 µM to 100 µM should be aimed for, preferably in the range from 0.01 µM to 10 µM. Those of skill in the art are able to determine dosages suitable to achieve such serum levels of inhibitor. Where the enhancer compound is a hexosaminidase inhibitor, serum levels of inhibitor should be monitored to avoid reaching inhibitory levels which will reduce hexosaminidase activity once it enters the lysosome, or to signal that inhibitory levels have been reached, in which case administration of the inhibitory compound may be reduced. Serum inhibitor levels may be monitored, for example, using the method described by Conzelman et al., (1982), Eur. J. Biochem., v. 123, p. 455). Similar monitoring can be used for other enzymes.

In a further aspect of the invention, the screening method described herein has identified compounds which may be used as probes for examination of cellular pathways and metabolism. For example, compound MAC 31850 has been identified as an inhibitor of hexosaminidase. It is a fluorescent compound which binds to hexosaminidase and therefore provides a fluorescent probe for monitoring the biosynthesis and localisation of the enzyme within a cell or for examining the folding of the enzyme in vitro.

In a further embodiment of the invention, the real time assay of hexosaminidase activity may be employed in a screening method for hexosaminidase activity-enhancing compounds employing cultures of cells which express a hexosaminidase of compromised or reduced activity. For example, cells expressing a mutant enzyme may be used, such as cells or cell lines from a patient with chronic Tay Sachs disease, which have a mutation in the alpha sub unit of hexosaminidase A or cells or cell lines from a patient with Sandhoff disease, which have a mutation in the beta sub unit of hexosaminidase A. Such cell lines are available, for example from Coriell cell line repository.

This assay will identify not only compounds which enhance hexosaminidase activity by direct interaction with the enzyme, either with the active site or other part of the molecule, but also compounds which affect hexosaminidase activity indirectly within the cell. This assay may be applied to any other enzyme whose activity can be monitored directly in the intact or lysed cell using an MU-containing substrate, for example the enzymes of Table 1.

In a further embodiment, a real time screen of candidate compounds has been carried out using cells which show reduced glucocerebrosidase (GCC) activity, as found in Type III Gaucher disease, employing as substrate MU-glucopyranoside. Miglitol, a compound previously use to treat adult on-set diabetes, was found to inhibit GCC. It was also found to inhibit alpha-glucosidase which is deficient in Pompe disease.

The invention provides a method of treating Gaucher disease or Pompe disease comprising administering to a subject in need of treatment an effective amount of miglitol.

EXAMPLES

Example 1

Real Time Monitoring of Hexosaminidase a Activity

25 µl Human hexosaminidase A (Hex A), isolated from human placenta and purified to greater than 95% homogeneity, at 1 ng/ml was diluted into 10 mM Citrate Phosphate buffer pH 4.3 containing 0.01% Human serum albumin. An equal volume of MUG (at different concentrations from 0.05 mM-1.6 mM) in 10mM Citrate Phosphate buffer pH 4.3 was added. The reaction was carried out at room temperature using excitation filters at 330 nm and emission filter set to 465 nm and monitored for ~5 minutes.

FIG. 1A shows the activity of purified human hexosaminidase A 1 ng/ml at various concentrations of MUG. FIG. 1B shows that this method indicates a Km value similar to the published Km for MUG. At high MUG concentrations, substrate inhibition is 25 observed.

(1) dashed line: data fit to classical Michaelis-Menton kinetics:

(2) solid line: data fit to $$v = \frac{V_{max} \cdot [S]}{K_m + [S]}$$

classical kinetics with substrate inhibition:

$$v = \frac{V_{max} \cdot [S]}{K_m + [S] + \left(\frac{[S]^2}{K_i}\right)}$$

Example 2

A primary high throughput screen of a library of close to 1000 compounds was carried out using the method of the invention to identify compounds with hexosaminidase A inhibitory activity. The screen was performed at the McMaster High Throughput Screening Laboratory against 960 small molecules from the Maybridge P1000 library.

384-well plates were used and reagents were added using the Beckman-Coulter Integrated Robotic System. Fluorescence was read continuously using an analyst HT (Molecular Devices Corporation) plate reader. Each compound was tested in a single well at a single concentration of 20 µm.

Hex A Activity

Human N-acetyl-β-hexosaminidase A (HexA) activity was measured by continuous monitoring of release of the 4-methylumbelliferone fluorophore from 4-methylumbelliferone-N-acetyl-β-D-glucosamine (MUG). Excitation and emission wavelengths for detection were 330 nm and 450 nm respectively.

Software

Instrumentation:
  Core System: SAMI, V3.5 (Beckman-Coulter).
  BIOMEK™ FX: BIOMEK™ FX, V2.5c (Beckman-Coulter).
  ORCA: ORCA NT, V1.5a (Sagian/Beckman-Coulter).
  Analyst HT: Criterion Host, V2.00.11 (Molecular Devices Corporation).

Data Analysis:
  SOFTmax PRO, V4.6 (Molecular Devices Corporation).
  Microsoft Excel, Xlfit V2.08 (ID Business Solutions Limited).

Reagents

Enzyme: Human placental hexosaminidase A affinity purified to 95% purity
Buffer system: ca. 20 mM citrate/phosphate buffer pH 4.3 (Sigma).
Substrate: 4-methylumbelliferone-N-acetyl-β-D-glucosamine(MUG)
Inhibitor: NAG-thiazoline (NAG-T)
Small Molecule Library: 960 compounds from Maybridge; average molecular weight=325 g/mol A 384—well plate was used, outer columns of wells containing high control (enzyme alone) or low control (enzyme+ NAG-thiazoline) samples and inner columns of wells containing test samples.

Data Analysis

Identification of Hits

Each enzymatic reaction was read in the Analyst HT every 105 seconds for 12.25 minutes.

Enzymatic activity was calculated with SOFrmax Pro by the slope of the 5 data points between 105-525 s (inclusive).

Percent residual activity was calculated in Excel as:

$$\left[\frac{\text{Sample data} - \text{Mean of low controls}}{\text{Mean of high controls} - \text{Mean of low controls}}\right] \times 100$$

A compound was declared a 'hit' if it reduced the percent residual activity of HexA below the cutoff value of 70% in both replicate trials. This cutoff was calculated as 3× the average standard deviation of the high controls. % residual activity was % of uninhibited high control activity remaining in presence of test compounds Treatment of Outliers An outlier was defined as a compound which resulted in a residual activity of HexA that was lower than the cutoff value for one replicate, and greater than the cutoff for the other replicate; these should be retested.

Z and Z′ Calculations

Values for Z and Z′ were calculated as follows:

Where σ and µ are the standard deviation and mean respectively, of the sample (S), low control (L) and high control (H).

$$Z = 1 - \frac{3\sigma_S + 3\sigma_L}{\mu_S - \mu_L} \qquad Z' = 1 - \frac{3\sigma_H + 3\sigma_L}{\mu_H - \mu_L}$$

TABLE 2

Concentration and volumes of stock solutions in assay reactions.

| Reagent[†] | Reagents included in High controls[‡] | Reagents included in Low controls[‡] | Reagents included in Sample reactions[‡] | Initial Concentration | Volume Added | Final Concentration |
|---|---|---|---|---|---|---|
| HexA | X | X | X | 10 nM in 0.025% HSA (w/v) | 5 µL | 1 nM in 0.0025% HSA (w/v) |
| MUG | X | X | X | 75 µM | 39 µL | 58 µM |
| Library compounds | | | X | 1.0 mM | 1 µL | 20 µM |
| Citrate/phosphate buffer | X | | X | ca. 20 mM | 5 µL | ca. 20 mM* |
| NAG-T | | X | | 3.6 mM | 5 µL | 360 µM |
| DMSO | X | X | | neat | 1 µL | 2% (v/v) |

[†]HexA was kept at ca. 4° C. by the use of a cooling jacket and circulating bath of 60% glycerol. All other reagents were at room temperature.
[‡]Total assay volume per well = 50 µL
*All aqueous solutions were made in ca. 20 mM citrate/phosphate buffer, pH 4.3.

Calculations

Values of Z and Z

Values of Z and Z' were calculated only with the exclusion of 2 high control data points.

TABLE 3

Values of Z and Z' for the screening of HexA against Maybridge P1000.

| Replicate | Z | Z' | % Standard Deviation of Data | | |
|---|---|---|---|---|---|
| | | | Sample Data | High Controls | Low Controls |
| First | 0.18 | 0.61 | 25.7 | 11.6 | 1.2 |
| Second | 0.45 | 0.74 | 17.2 | 7.4 | 1.2 |

Graphical Representation of Data

Figure 10:
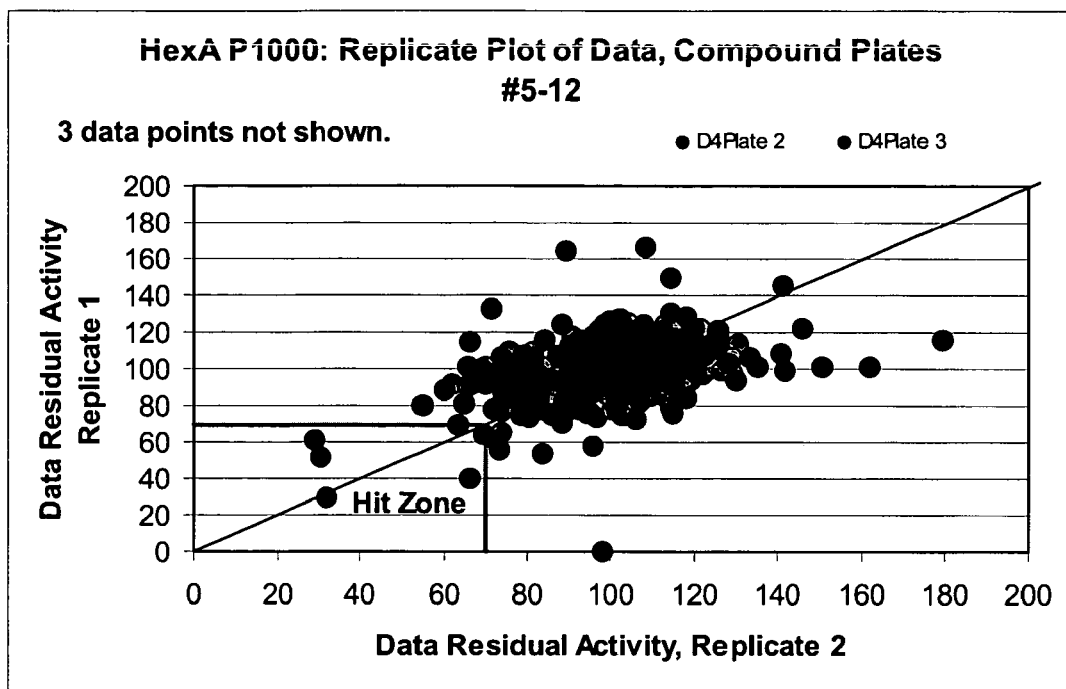
FIG. 10 shows residual hexosaminidase activity of Replicate 1 plotted against the same activity of Replicate 2.

FIG. 10 graphically presents the data of Hexosaminidase A screened against the Maybridge P1000 library, comparing replicated 1 and 2.

Example 3

A similar screen was carried out of 37,440 compounds from a Maybridge small molecule library. Each compound was tested singly at a single concentration—10 μm. The threshold for further investigation was selected as 80% residual hexosaminidase A activity. By this method, 64 compounds were identified as meriting further investigation. The inhibitory compounds shown in Table 5 were identified by this screen.

TABLE 4

IC50's were determined in 384-well format using the following reagent additions:

| Reagent[†] | [Initial] | Volume Added | [Final] |
|---|---|---|---|
| HexA with | 0.5 μg/mL HexA | 10 μL | 100 ng/mL HexA |
| HSA (2) | 0.0125% (w/v) HSA | | 0.0025% HSA (w/v) |
| MUG (3) | 75 μM | 39 μL | 58.8 μM |
| Hits (1) | 5.2 μM-5 mM | 1 μL | 0.104 μM-100 μM |

[†]Numbers in brackets indicate order of addition to assay.

Figure 14:
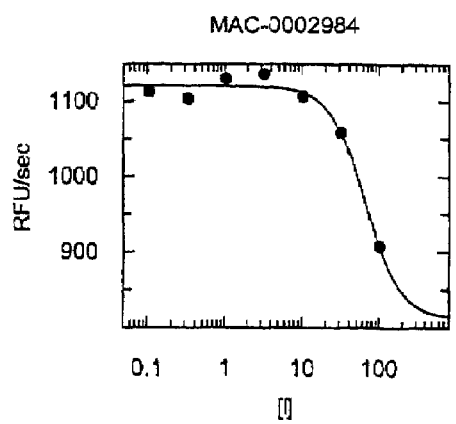
FIGS. 14A-14X show IC50 plots for inhibition of GCC by various compounds.
Figure 14:
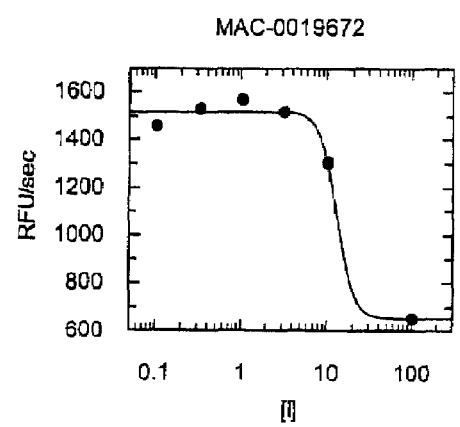
Figure 14:
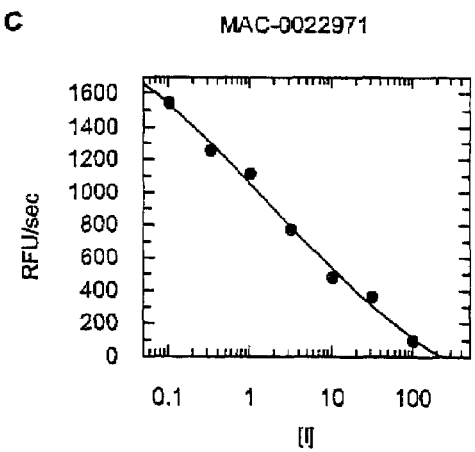
Figure 14:
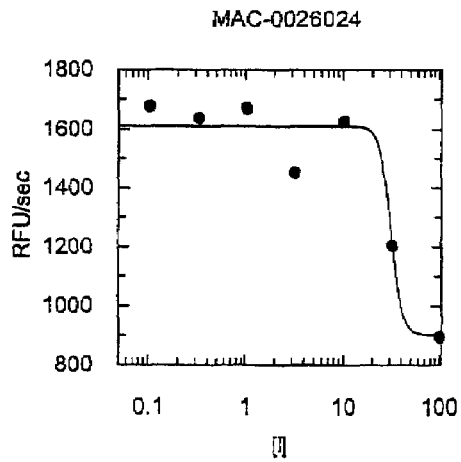
Figure 14:
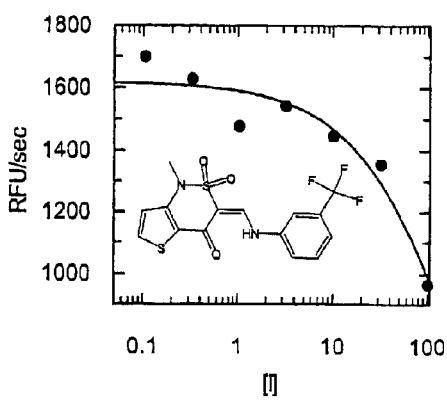
Figure 14:
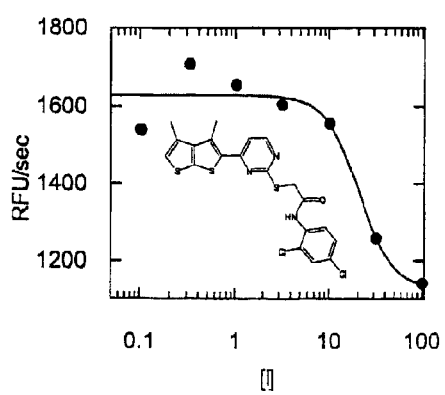
Figure 14:
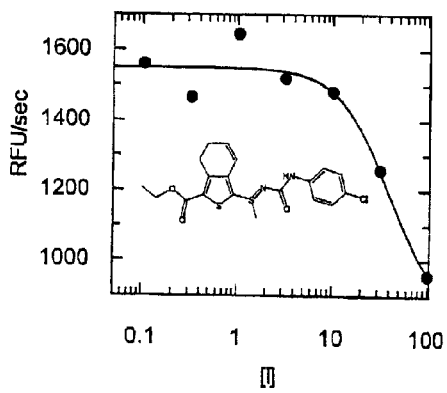
Figure 14:
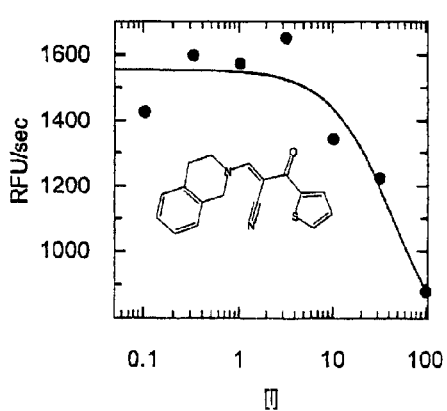
Figure 14:
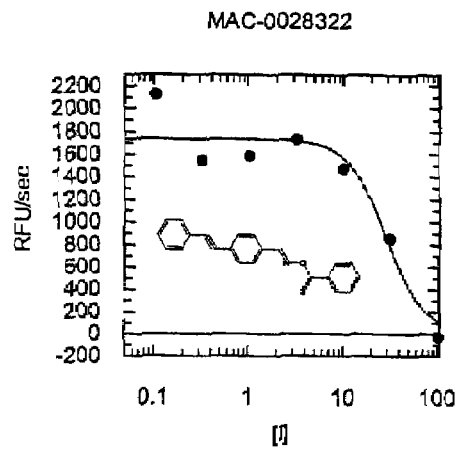
Figure 14:
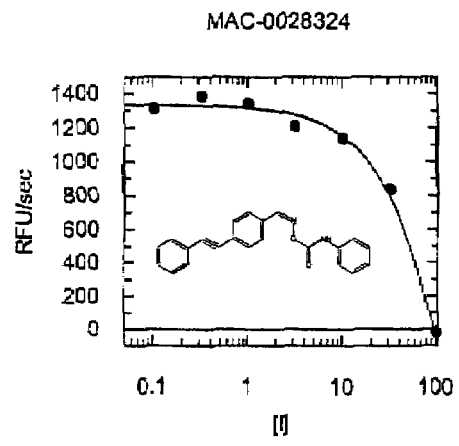
Figure 14:
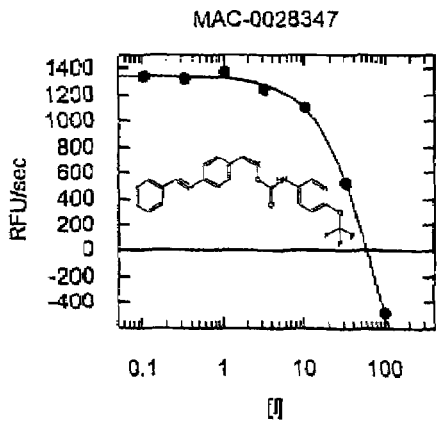
Figure 14:
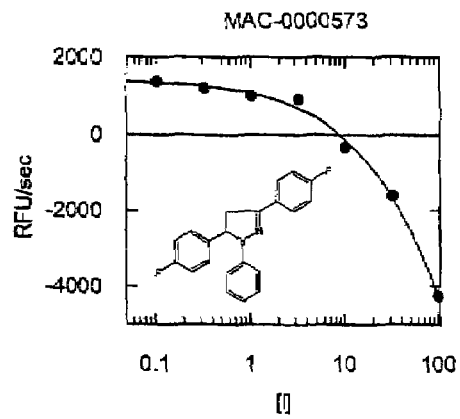
Figure 14:
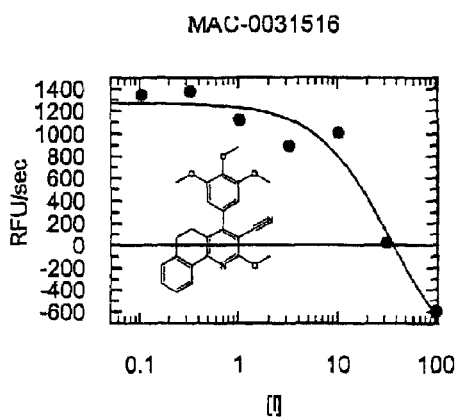
Figure 14:
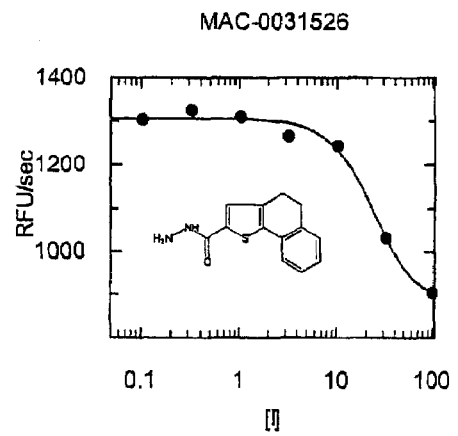
Figure 14:
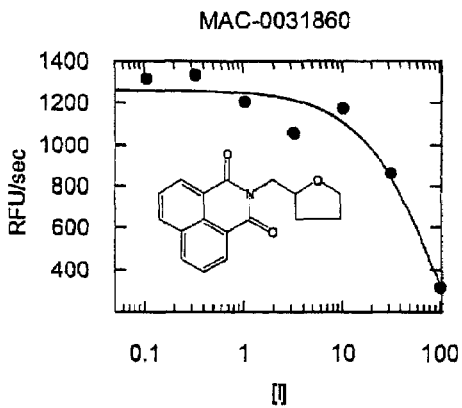
Figure 14:
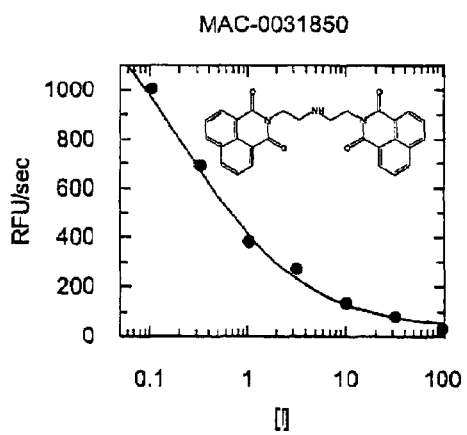
Figure 14:
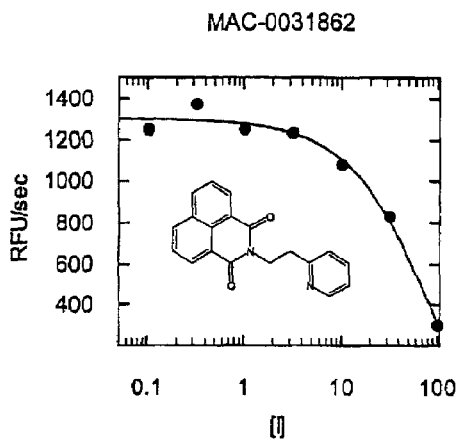
Figure 14:
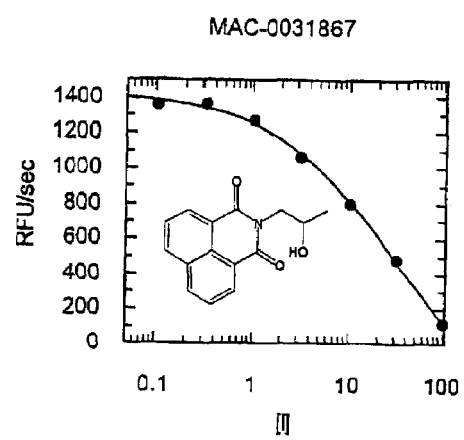
Figure 14:
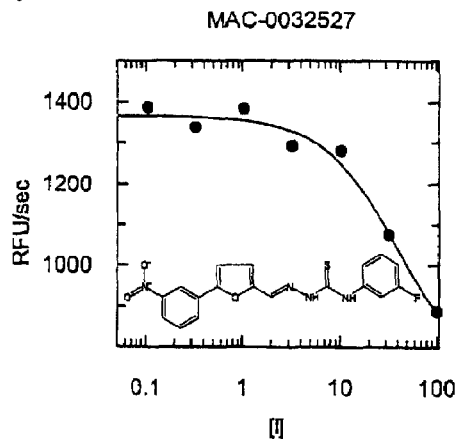
Figure 14:
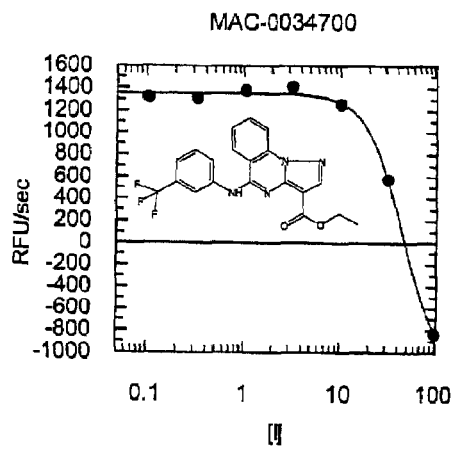
Figure 14:
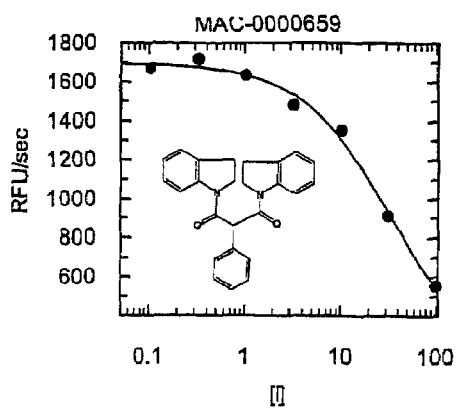
Figure 14:
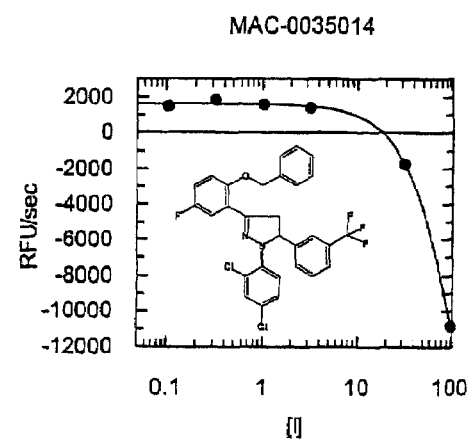
Figure 14:
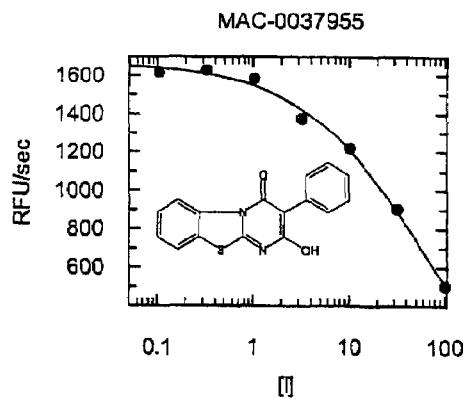
Figure 14:
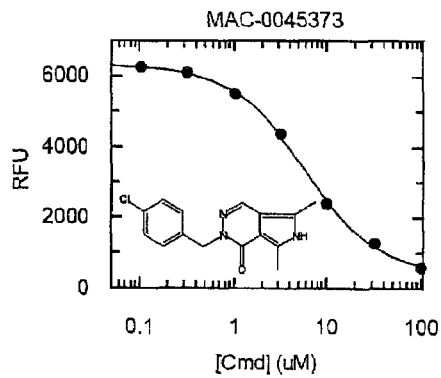

IC50 plots were generated in Excel; 'well behaved' hits were defined as those resulting in the characteristic sigmoidal semi-logarithmic plot;

Data for well behaved compounds were replotted in GraFit and IC50's determined using $$y = \frac{Range}{1 + \left(\frac{x}{IC_{50}}\right)^s} + Background$$

where Range=the fitted uninhibited value minus the background and s is a slope factor; the results are shown in FIG. 14.

Example 4

Figure 3:
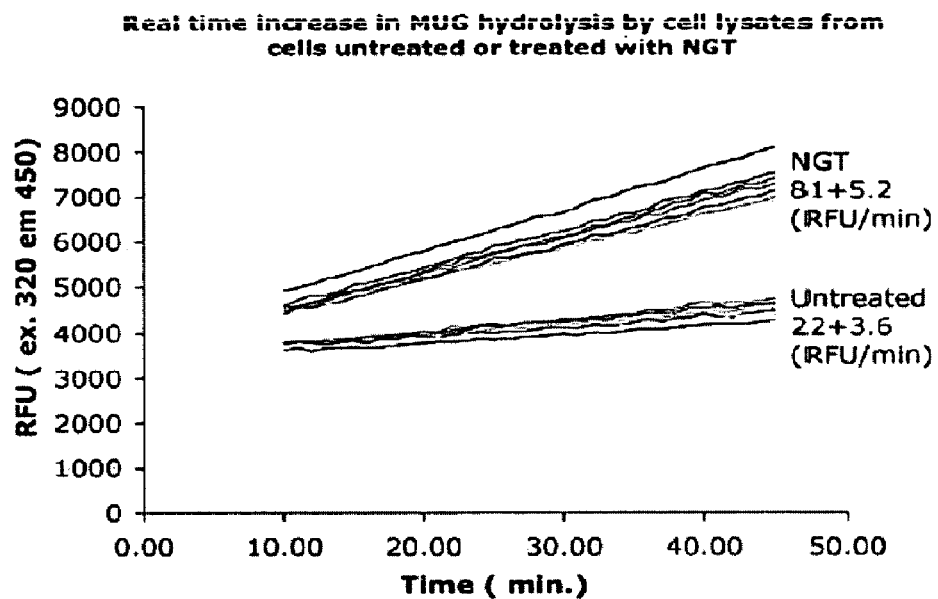
FIG. 3 shows graph of MUG hydrolysis against time for cell lysates from cells untreated or treated with NGT.

294 (Infantile Sandhoff Disease) cells in 96 well tissue culture plate were grown for 2-5 days at 37° C. to 25-50% confluency in alpha mem medium supplemented with 10% FCS lacking or containing NGT (1 mM). For real time assay hexosaminidase A, medium was removed, cells were washed twice with phosphate buffered saline, and lysed with 70 μl of 10 mM Na Phosphate buffer pH 6.8 containing 0.1% Triton X-100, 0.025% human serum albumin for 15 minutes at room temperature. A 25 μl aliquot of the lysate was transferred to a fresh 96 well polystyrene plate. The reaction was initiated by addition of an equal volume of 3.2 mM MUG substrate in 50 mM Citrate Phosphate buffer pH 4.3. The reaction was monitored in real time at 37° C. for 1 hour using the Molecular Devices Gemine EM Max Fluorimeter with excitation set to 330 nm and emission set to 460 nM. FIG. 3 shows the rate of MUG hydrolysis by cell lysates from 294 (ISD) cells treated with NGT(1 mM) or untreated, in 15 quintuplicate. It can be seen that NGT enhances hexosaminidase activity.

Example 5

Treatment of ISD Cells with Compounds Identified by Screen

ISD cells in 96 well tissue culture plate were grown for 2-5 days at 37° C. to 25-50% confluency in alpha mem meda supplemented with 10% FCS lacking or containing GalNAc Thiazoline (GalNAct), GlcNAc Thiazoline (NGT), compound MAC-0028347, MAC-00659, MAC-0022971, MAC0045373 or MAC-0031850 (MAC compounds were hit compounds from screen of Example 3). All compounds were evaluated at 4 different concentrations (~1 mM, 0.3 mM, 0.1 mM and 0.3 mM). For endpoint assay, medium was removed, cells were washed twice with phosphate buffered saline, and lysed with 70 μl of 10 mM Na Phosphate buffer pH 6.8 containing 0.1% Triton X-100, 0.025% human serum albumin, for 15 minutes at room temperature. Two 25 μl aliquots of the lysate were each transferred to separate 96 well polystyrene plates. The reaction was initiated by addition of an equal volume of 3.2 mM MUG substrate or methyl umbelliferyl phosphate (MUP) in 50 mM Citrate Phosphate buffer pH 4.3. The reaction was carried out 37° C. for 30 minutes, subsequently 200 μl of 0.1M MAP pH 10.5 was added to stop the reaction. Fluorescence was read using an Molecular Devices Gemine EM MAX Fluorimeter with excitation set to 365 nm and emission set to 460 nM.

Figure 4:
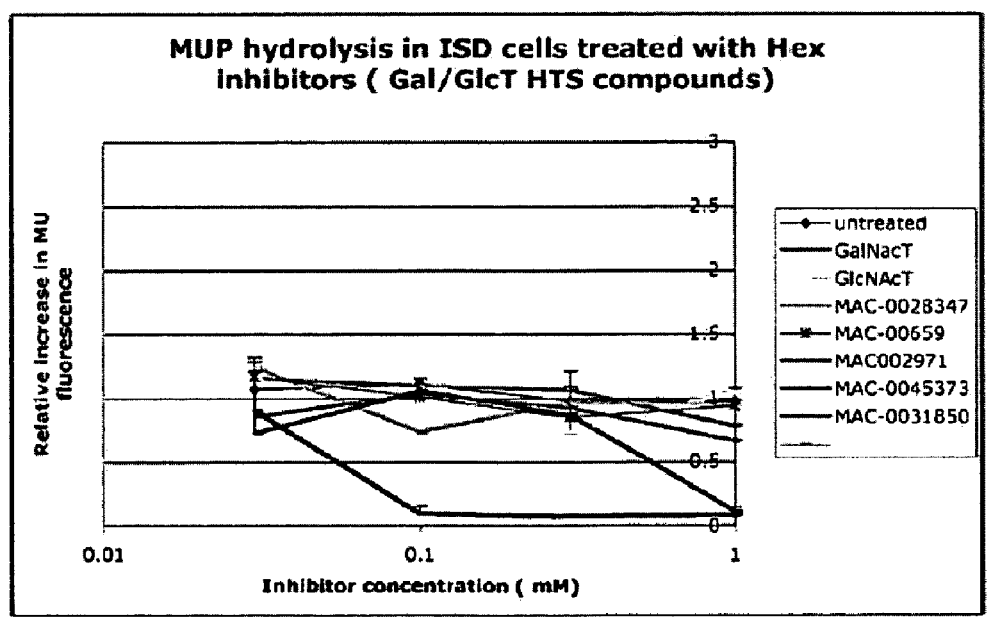
FIG. 4 shows graph of relative increase in enzyme activity (MU fluorescence) at various concentrations of the indicated inhibitors.
Figure 5:
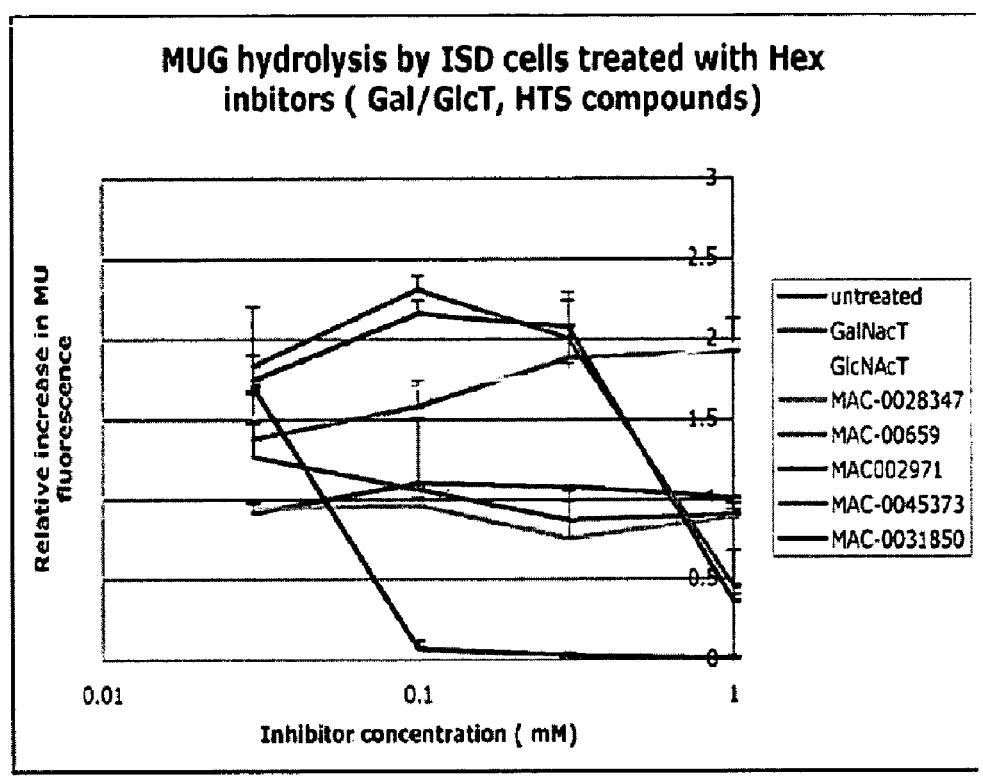
FIG. 5 shows graph of relative increase in enzyme activity (MU fluorescence) in the presence of various concentrations of the indicated inhibitors.

The results are shown in FIGS. 4 and 5.

MUP, which is a substrate for acid phosphatase, which should not be inhibited by hexosaminidase inhibitors, was used as a general indicator of toxicity. Compounds 0045373 and 00659 gave good enhancement of hexosaminidase activity. 0045373 had an IC50 of 5.4±0.44 μm and 00659 had an IC50 of 34±21 μm.

Example 6

The compounds of the P1000 library (Maybridge plc, Cornwall, UK) were screened for their effect on the activity of human glucocerebrosidase (GCC) by the method of the invention in duplicate in 384-well plate format. The screen was fully automated on a SAIGAIN core system (Beckman-Coulter Inc., Fullerton, Calif.) with an ORCA arm for labware transportation, a Biomek FX for liquid handling, and an Analyst HT (Molecular Devices Corp., Sunnyvale, Calif.) for fluorescence detection ($\lambda_{ex}$=330 nm; $\lambda_{em}$=460 nm).

TABLE 6

Assay reagents in order of addition to reaction.

| Solution | Components[b] | Initial concentration | Volume added | Final concentration |
|---|---|---|---|---|
| (1) Test compound[a] | (i) DMSO | neat | 1 μL | 2% (v/v) |
| | (ii) Cast | 0.5 mg/mL | | 0.01 mg/mL |
| | (iii) Cmd Library | 1 mM | | 20 μM |
| (2) Enzyme mix | GCC | 0.15 mg/mL | 24 μL | 72 μg/mL |
| | TC | 0.5% (w/v) | | 0.24% (w/v) |
| | HSA | 0.1% (w/v) | | 0.048% (w/v) |
| (3) Substrate mix | Glc-MU | 1.25 mM | 25 μL | 625 μM |
| | HSA | 0.1% (w/v) | | 0.048% (w/v) |

[a]High and low controls and the sample assays contained one each of (i), (ii) and (iii) respectively.
[b]TC, taurocholate; HSA, human serum albumin; Glc-MU, 4-methylumbelliferyl-β-D-glucopyranoside; DMSO, dimethylsulfoxide; Cast, castanospermine; Cmd, compound.

Table 6: Assay reagents in order of addition to reaction.

All liquid handling and activity detection was done at room temperature. Each 384-well assay plate was read 9 times, with 105 s between each read. Reaction rates (RFU/sec) were calculated as the slope of the data of the second to ninth data point, inclusive. For the compounds screened, Z' averaged 0.6

Tables 7 & 8 show the compounds which reduced GCC activity by more than 65%. R1 and R2 are replicate results, expressed as % residual enzyme activity.

Example 7

The method of the invention was used in a cell based assay, using MUG as substrate, to identify compounds which directly increase Hex S activity in fibroblasts (ISD 294 cell line) from a patient with the infantile form of Sandhoff disease (homozygous Null mutation in Hex alpha-subunit).

Compounds which increase Hex S in these cells may do so using one of three mechanisms, (1) by binding to the active site and acting as a pharmacological chaperone and enzyme inhibitor, (2) by binding binding elsewhere on the enzyme and stabilizing the enzyme through its action as a specific chemical chaperone or 3) by an indirect pathway e.g. increasing the transcription from the Hex gene or affecting some aspect of the quality control pathway in the endoplasmic reticulum. Compounds can be differentiated in terms of their mechanism of action using two different enzyme assays. Compounds which stabilize using mechanism 1 will also function as inhibitors in the in vitro MUG enzyme assay, whereas mechanism 2 and 3 compounds will not. In contrast, compounds enhancing Hex S levels by mechanism 1 or 2 will attenuate thermal denaturation of Hex at elevated temperatures, whereas mechanism 3 compounds will not.

The NINDS Custom collection of 1040 biologically active compounds from Microsource Discovery Systems, Inc. as described on the MicroSource Discovery Systems, Inc. website (Rothstein et al. Nature 433:73 (2005)) was used to treat the ISD 294 cell line which had been plated into 96 well tissue culture plates (2000-5000 cells per well). The two outside columns (1 and 12) of the plate were used for negative controls (DMSO) and positive controls (DMSO and NGT 0.9 mM) placed in alternating wells. Previously we have shown that NGT enhances Hex S in 294 cells 3-6x relative to DMSO (mock) treated cells. Columns 2-11 have compounds from the NINDS collection added to the cells with media (alpha mem 10% fetal calf serum) to a final concentration of 50 μM (0.5% DMSO). Cells were incubated in the presence of the compounds for 3 days at 37° C. in a $CO_2$ humidified incubator. All treatments were performed in duplicate.

Figure 6:
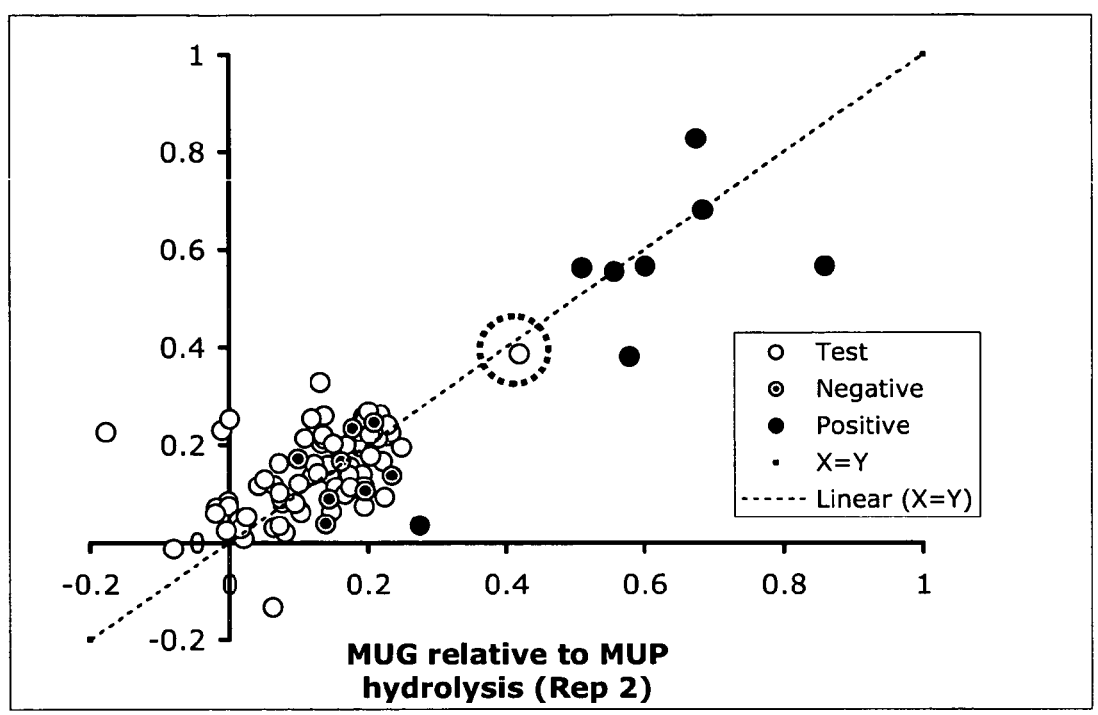
FIG. 6 shows graph of MUG activity relative to MUP activity in 294 cells treated with NGT (solid circles), DMSO (shaded circles) or compounds from NINDS collection (open circles).

To determine which of the compounds enhanced HexS activity, following the 3 day incubation, medium was aspirated and the cells were washed twice with Phosphate buffered saline. Cells were lysed using citrate-phosphate buffer (10 mM), pH 5, 0.3% human serum Albumin and 0.1% triton X-100. Hydrolysis of MUG and 4-methylumbelliferyl phosphate substrates (MUP), were monitored in real-time fluoremetrically, as described in Example 1, in order to measure Hex S and acid phosphatase activity, respectively. To control for variability of cell number, Hex S (MUG) activity was expressed relative to acid phosphatase (MUP) activity. Values from the two replicates were plotted (FIG. 6) and only those compounds which replicated (were in the vicinity of x=y) were considered for further analysis. The majority of compounds had no effect i.e. they were coincident with DMSO treated negative control ( grey circles).

Figure 7:
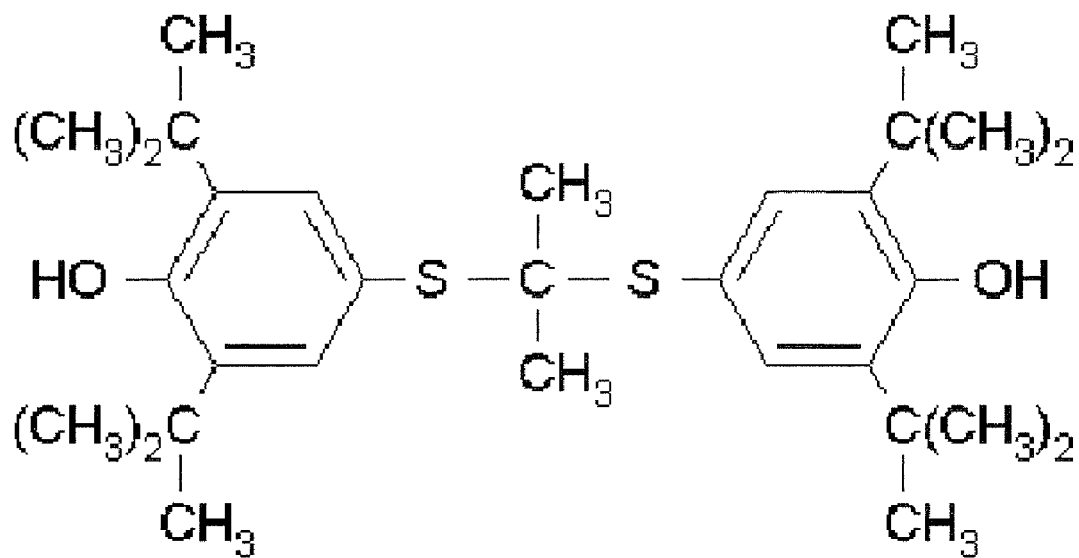
FIG. 7 shows the structure of probucol.
Figure 8:
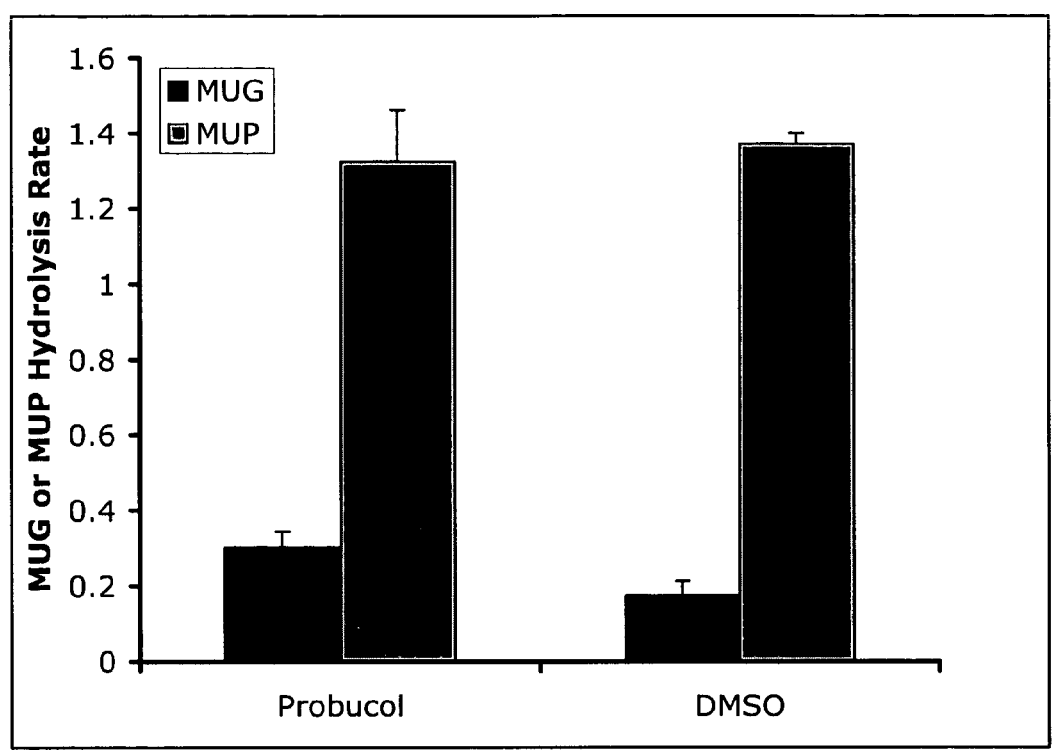
FIG. 8 shows the hydrolysis rate of MUG (solid bars) or MUP (shaded bars) in 294 cell lysates in the presence of probucol or DMSO.

One compound, probucol (FIG. 7), approached ( dashed circle) the relative MUG activities found in 294 cells treated with NGT ( positive control ( black circles). Re-evaluation of this compound using a new batch of cells, confirmed the enhancing of effect ( ca 2 fold) of probucol on MUG activity in 294 cells (FIG. 8). This compound did not inhibit Hex activity, as no significant effect on Hex activity was observed at the highest soluble concentration of probucol (100 μM). This compound is therefore unlikely to be binding to the active site of the enzyme and may be enhancing Hex activity by either binding outside the active site or by some other mechanism.

Probucol is an FDA approved anti-oxidant drug for use in the treatment of atherosclerosis (Pfuetze K D, Dujovne C A., Current Atherosclerosis Rep. 2000 January; 2(1):47-57.) by increasing the uptake of high density lipoprotein cholestryl esters (Ohya T, Egusa G.Nippon Rinsho. 1999 December; 57(12):2831 -6).

Example 8

Figure 9:
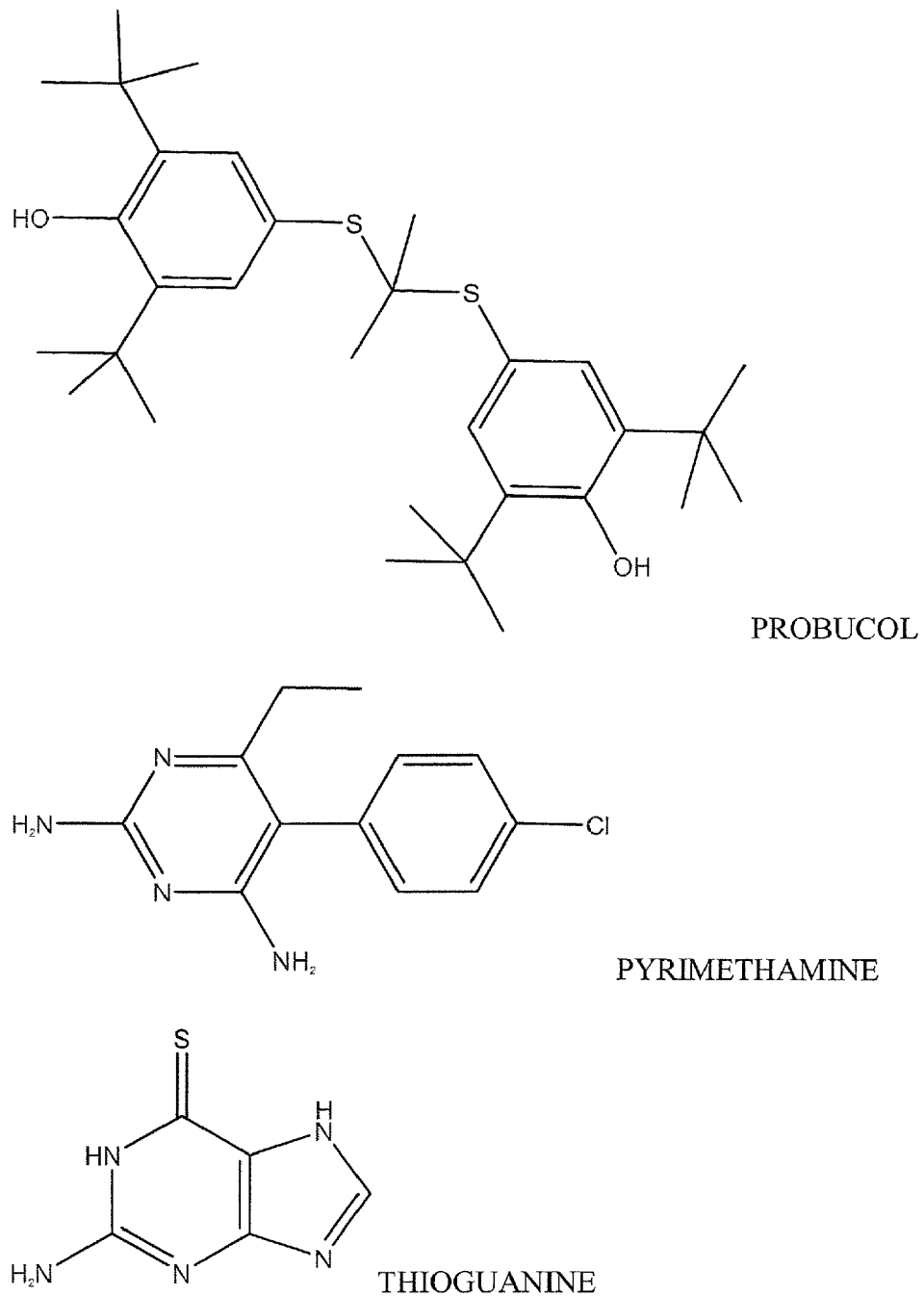
FIG. 9 shows the structure of the indicated compounds.
Figure 11:
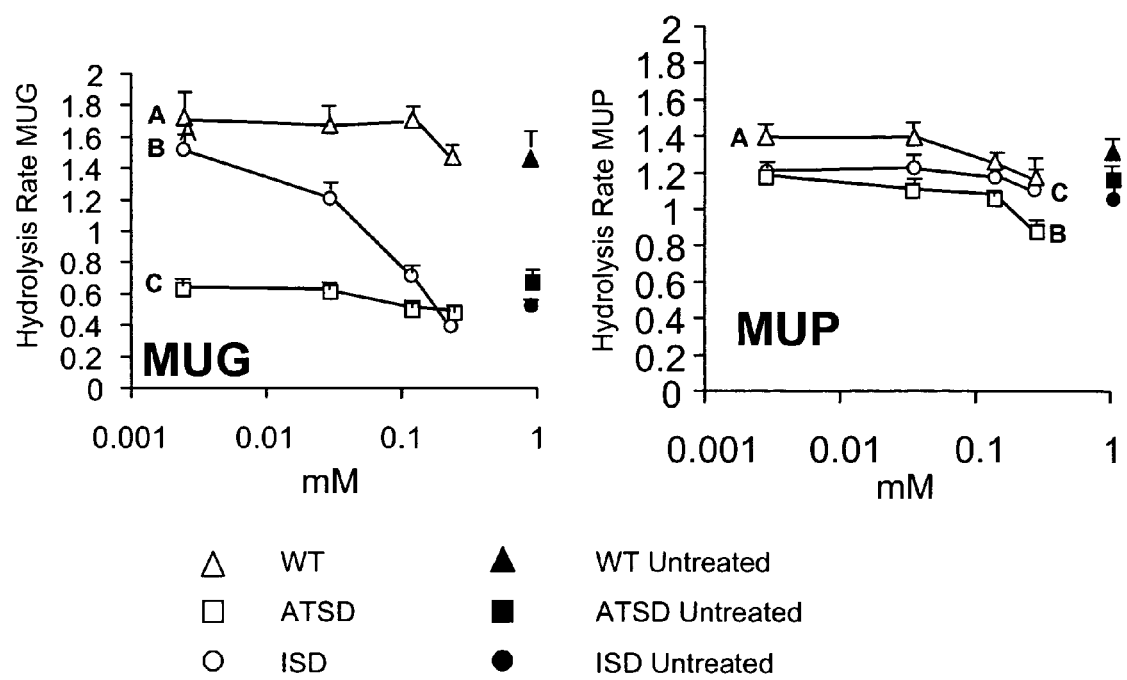
FIG. 11 shows rate of hydrolysis of MUG or MUP by the indicated cell lines untreated or treated with pyrimethamine
Figure 12:
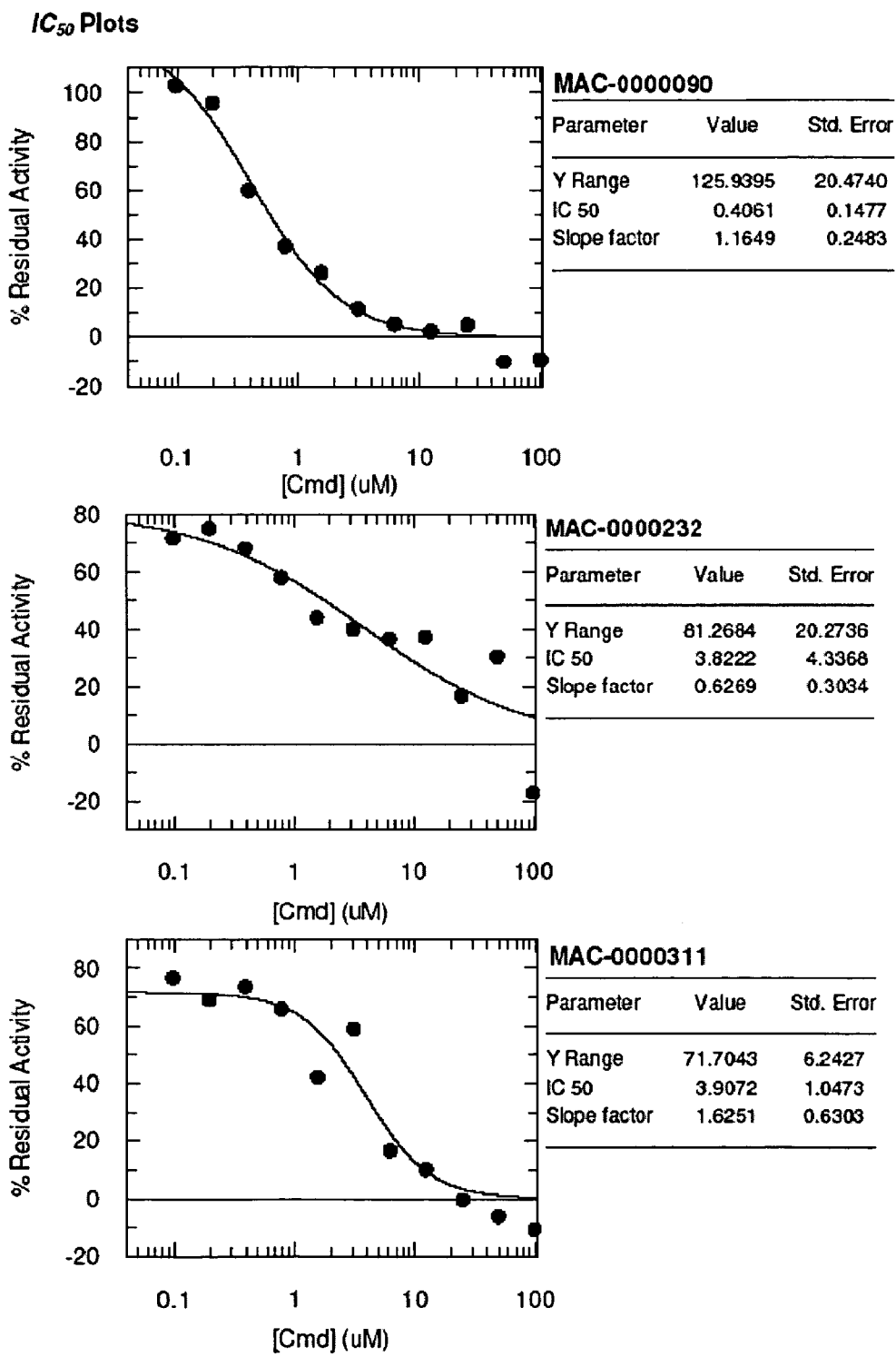
FIG. 12 shows IC50 plots for inhibition of GCC by various compounds.
Figure 12:
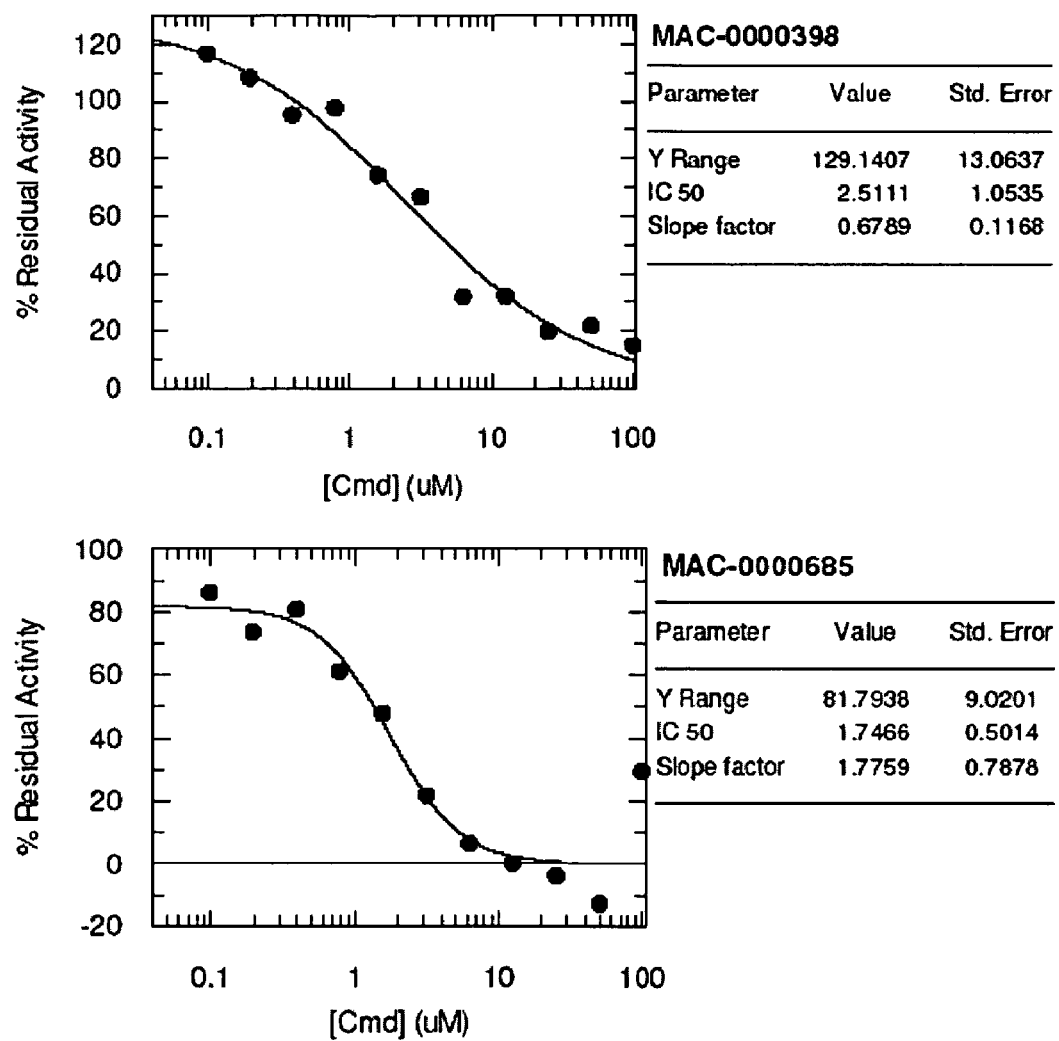

Using the same approach described in Example 2 for the screen of the Maybridge library, Hex A was re-probed with the NINDS collection of 1040 FDA-approved drugs for compounds which inhibited purified Hex A. Two compounds were identified, pyrimethamine (IC50 about 600 nm) and thioguanine. These compounds are shown in FIG. 9. A related compound, 2,6 diaminopurine, also inhibited Hex A (IC50 about 800 nm), and could function as a pharmacological chaperone. Pyrimethamine was shown to enhance the activity of Hex in adult Tay Sachs fibroblasts and infantile Sandhoff fibroblasts (FIG. 11).

Example 9

Figure 13:
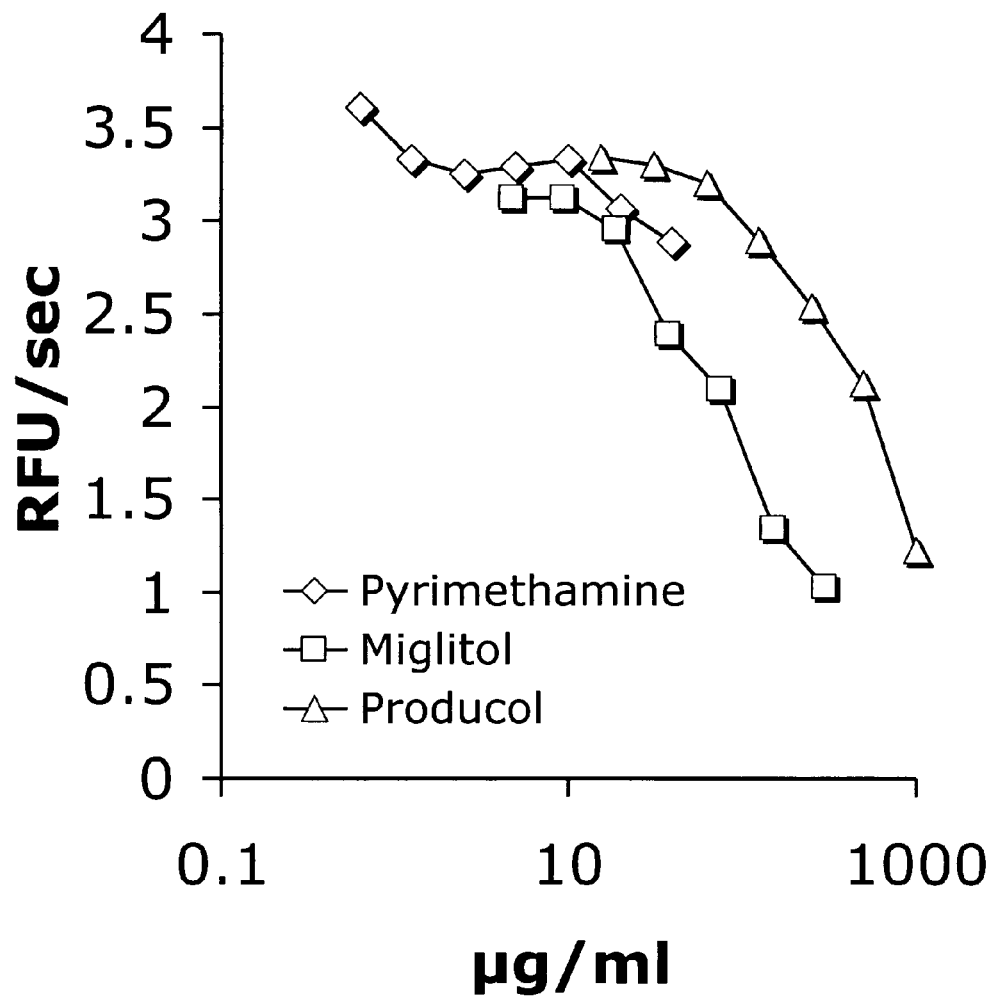
FIG. 13 shows a graph of inhibition of GCC by various concentrations of the indicated compounds.

A similar screen to that described in example 6 was carried out on compounds from the NINDS Custom collection. 23 GCC inhibitory compounds were identified (Table 9). 5 of the hit compounds from the Maybridge screen and 2 from NINDS Custom collection screen were further characterized as GCC inhibitors, using the real time MU-Glc substrate assay. The results are shown in FIG. 13. These compounds are potential pharmacological chaperones for the treatment of adult form Gaucher disease resulting from the most common mutant allele, N370S, in GCC. Miglitol is also an inhibitor of alpha-glucosidase and can also be used to treat late onset forms of Pompe disease where there is some residual enzyme activity.

TABLE 1

| ENZYME | DISORDER |
|---|---|
| Acetyl-CoA glcNAc Transferase | Sanfilippo Disease, type C |
| Acid lipase | Wolman/Cholesterol Ester Storage D. |
| Alpha-fucosidase | Fucosidosis |
| Alpha-galactosidase | Fabry Disease |
| Alpha-N-Acetylgalactosaminidase | Schindler Disease |
| Alpha-N-Acetylglucosaminidase | Sanfilippo Disease, type B |
| Alpha-glucosidase | Pompe Disease |
| Alpha-iduronidase | Hurler and Scheie Disease |
| Alpha-mannosidase | Alpha-Mannosidosis |
| Alpha-neuraminidase | Sialidosis, Galactosialidosis |

TABLE 1-continued

| ENZYME | DISORDER |
|---|---|
| Beta-galactosidase | GM1-gangliosidosis and Morquio B |
| Beta-glucosidase | Gaucher Disease |
| Beta-glucuronidase | Sly Disease |
| Beta-hexosaminidase A and B | GM2-gangliosidosis (Tay-Sachs, Sandhoff) |
| Beta-mannosidase | Beta-Mannosidosis |
| GalNAc 6-sulfate sulfatase | Morquio Disease, type A |
| GlcNAc 6-sulfate sulfatase | Sanfilippo Disease, type D |
| Heparan N-sulfatase | Sanfilippo Disease, type A |

TABLE 5

| Structure | code | product_name |
|---|---|---|
| 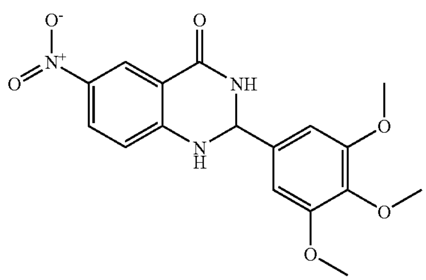 | BTB 01827 | 6-nitro-2-(3,4,5-trimethoxyphenyl)-1,2,3,4-tetrahydroquinazolin-4-one |
| 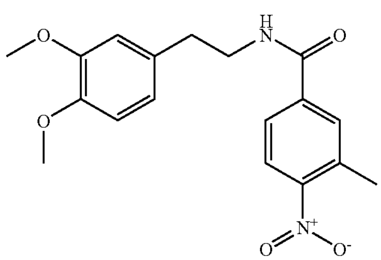 | BTB 01871 | N1-(3,4-dimethoxyphenethyl)-3-methyl-4-nitrobenzamide |
| 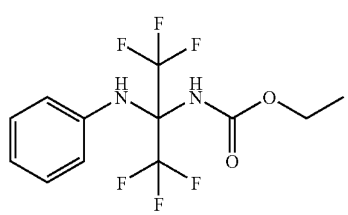 | BTB 14232 | ethyl N-[2,2,2-trifluoro-1-(pyrimidin-2-ylamino)-1-(trifluoromethyl)ethyl]carbamate |
| 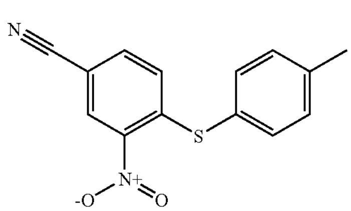 | CD 08015 | 4-[(4-methylphenyl)thio]-3-nitrobenzonitrile |

TABLE 5-continued

| Structure | code | product_name |
|---|---|---|
| 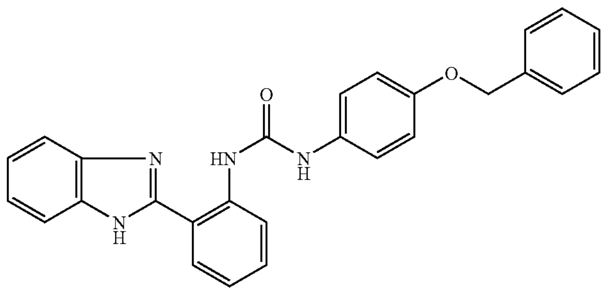 | HTS 05835 | 2-(1H-benzimidazol-2-yl)-N-[4-(benzyloxy)phenyl]benzamide |
| 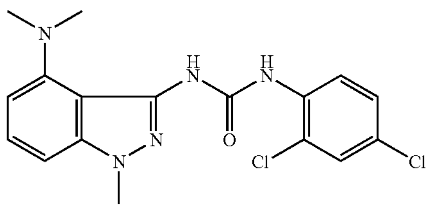 | HTS 05845 | N-(2,4-dichlorophenyl)-N'-[4-(dimethylamino)-1-methyl-1H-indazol-3-yl]urea |
| 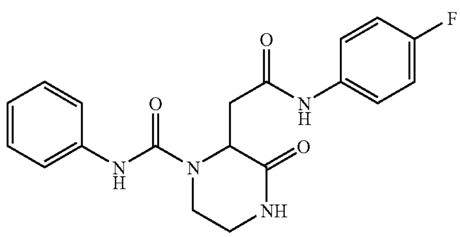 | HTS 05846 | 2-[2-(4-fluoroanilino)-2-oxoethyl]-3-oxo-N-phenyltetrahydro-1(2H)-pyrazinecarboxamide |
| 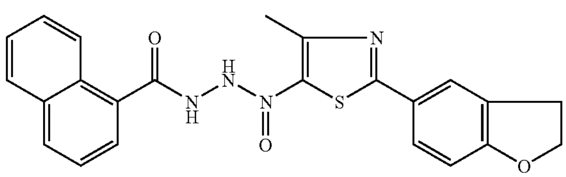 | HTS 07376 | N'-{[2-(2,3-dihydro-1-benzofuran-5-yl)-4-methyl-1,3-thiazol-5-yl]carbonyl}-1-naphtho hydrazide |
| 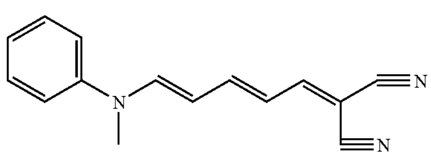 | JFD 00044 | 2-[5-(methylanilino)penta-2,4-dienylidene]malononitrile |
| 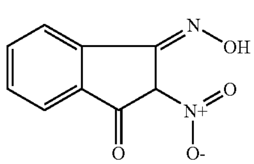 | JFD 02087 | 3-hydroxyimino-2-nitroindan-1-one |
| 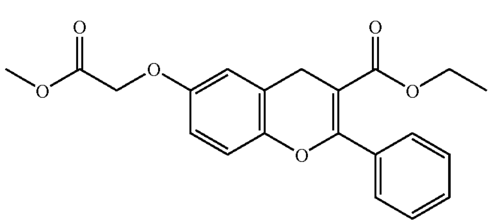 | JFD 02998 | ethyl 5-(2-methoxy-2-oxoethoxy)-2-phenyl-1-benzofuran-3-carboxylate |

TABLE 5-continued

| Structure | code | product_name |
|---|---|---|
| 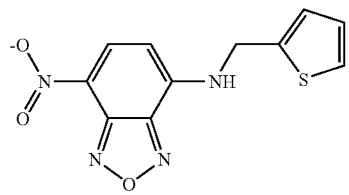 | KM 06825 | N4-(2-thienylmethyl)-7-nitro-2,1,3-adiazol-4-amine |
| 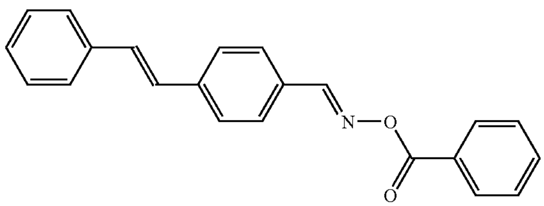 | KM 08092 | N-(benzoyloxy)-N-{[4-(2-phenylethynyl)phenyl]methylene}amine |
| 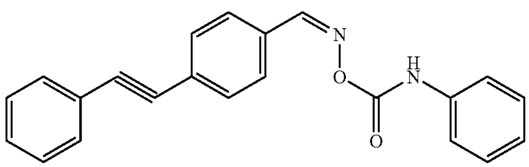 | KM 08094 | N-[(anilinocarbonyl)oxy]-N-{[4-(2-phenyl ethynyl)phenyl]methylene}amine |
| 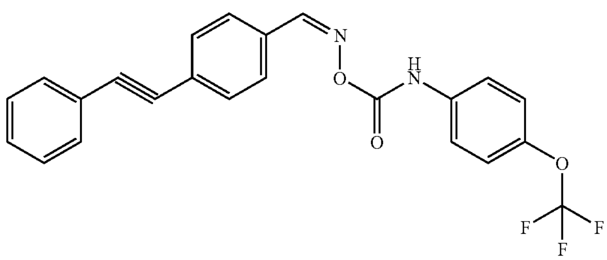 | KM 08120 | N-{[4-(2-phenylethynyl)phenyl]methytene}-N-({[4-(trifluoromethoxy)anilino]carbonyl}oxy)amine |
| 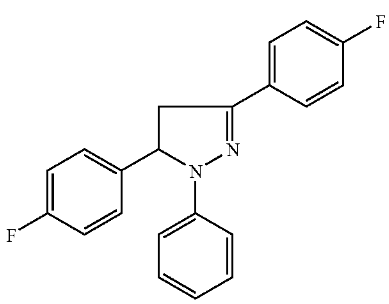 | PD 00289 | 3,5-di(4-fluorophenyl)-1-phenyl-4,5-dihydro-1H-pyrazole |
| 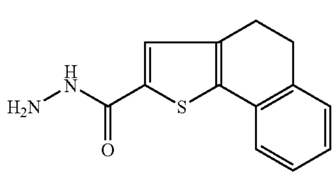 | PD 00633 | 4,5-dihydronaphtho[1,2-b]thiophene-2-carbo hydrazide |
| 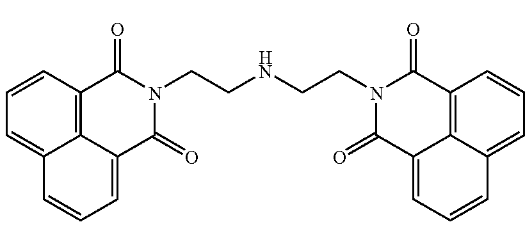 | PHG 00899 | 2-(2-{[2-(1,3-dioxo-2,3-dihydra-1H-benzo[de]isoquinolin-2-yl)ethyl]amino}ethyl)-2,3-dihydro-1H-benzo[de]isoqulnoline-1,3-dione |

TABLE 5-continued

| Structure | code | product_name |
|---|---|---|
| 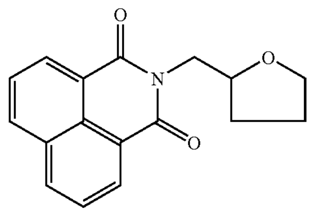 | PHG 00949 | 2-(tetrahydrofuran-2-ylmethyl)-1H-benzo[de]isoquinoline-1,3(2H)-dione |
| 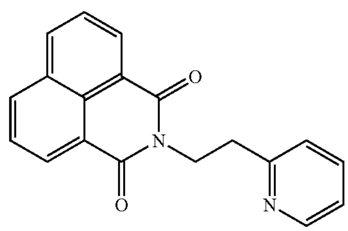 | PHG 00951 | 2-[2-(2-pyridyl)ethyl]-2,3-dihydro-1H-benzo[de]isoquinoline-1,3-dione |
| 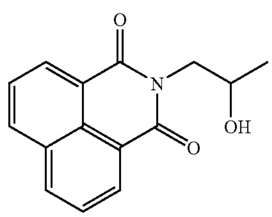 | PHG 00959 | 2-(2-hydroxypropyl)-1H-benzo[de]isoquinoline-1,3(2H)-dione |
| 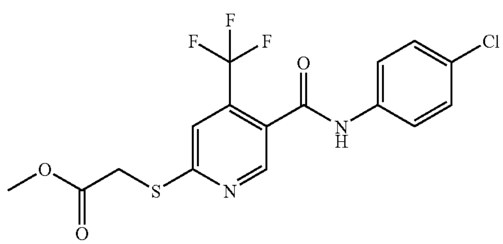 | RF 04442 | methyl 2-{[5-[(4-chloroanilino)carbonyl]-4-(trifluoromethyl)pyridin-2-yl]thio}acetate |
| 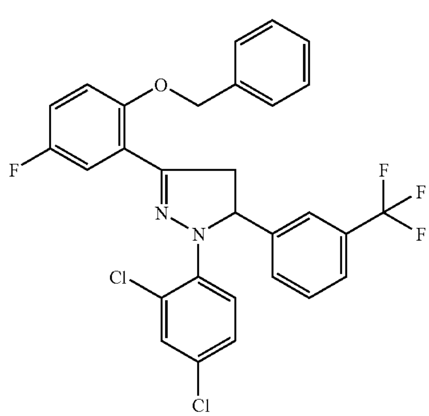 | RH 00631 | 3-[2-(benzyloxy)-5-fluorophenyl]-1-(2,4-dichlorophenyl)-5-[3-(trifluoromethyl)phenyl]-4,5-dihydro-1H-pyrazole |

TABLE 5-continued

| Structure | code | product_name |
|---|---|---|
| 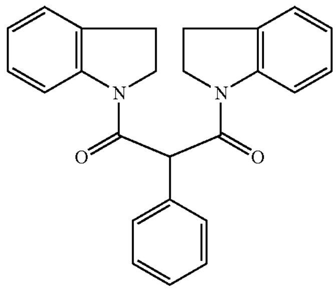 | RH 00659 | 1,3-di(2,3-dihydro-1H-indol-1-yl)-2-phenyl propane-1,3-dione |
| 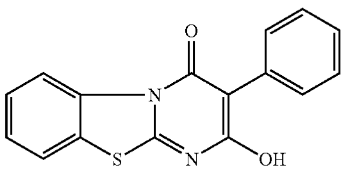 | RJC 03360 | 2-hydroxy-3-phenyl-4H-benzo[d]pyrimido[2,1-b][1,3]thiazol-4-one |
| 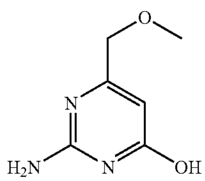 | RJF 00700 | 2-amino-6-(methoxymethyl)pyrimidin-4-ol |
| 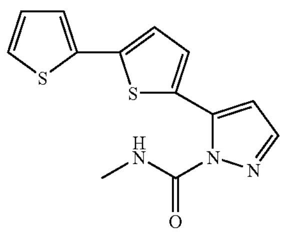 | SEW 02233 | 1-Methylaminocarbonyl-5-[5-(thiophen-2-yl)thiophen-2-yl]pyrazole |
| 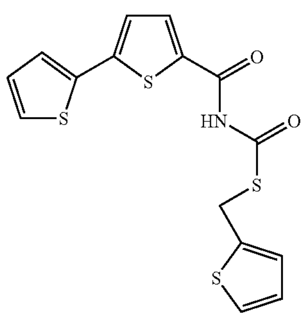 | SEW 02563 | 2-thienylmethyl ({[5-(2-thienyl)-2-thienyl]carbonyl}amino)methanthioate |
| 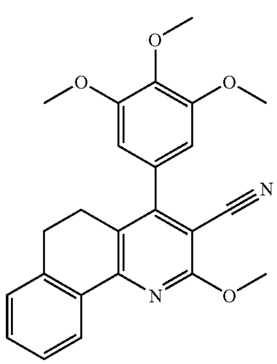 | PD 00623 | 2-methoxy-4-(3,4,5-trimethoxyphenyl)-5,6-dihydrobenzo[h]quinoline-3-carbonitrile |

TABLE 5-continued

| Structure | code | product_name |
|---|---|---|
| 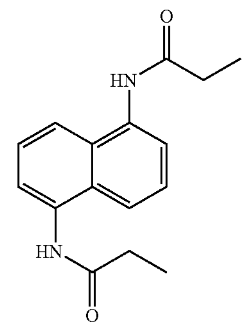 | JFD 00041 | N1-[5-(propionylamino)-1-naphthyl]propan amide |
| 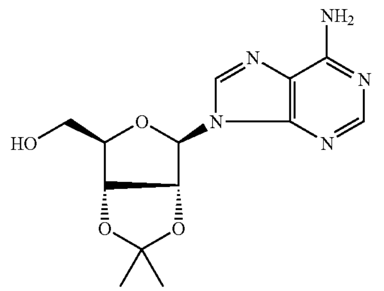 | RJC 03233 | [6-(6-amino-9H-purin-9-yl)-2,2-dimethyltetra hydrofuro[3,4-d][1,3]dioxol-4-yl]methanol |
| 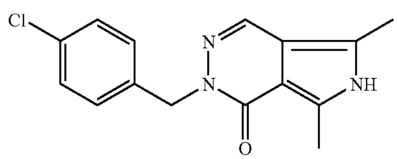 | SP 00124 | 2-(4-chlorobenzyl)-5,7-dimethyl-2,6-dihydro-1H-pyrrolo[3,4-d]pyridazin-1-one |
| 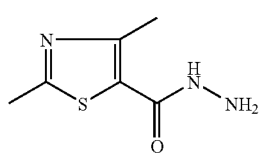 | SPB 01606 | 2,4-dimethyl-1,3-thiazole-5-carbohydrazide |
| 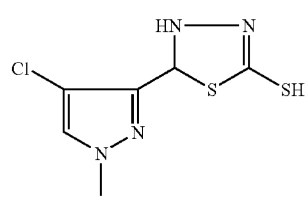 | SPB 06972 | 5-(4-chloro-1-methyl-1H-pyrazol-3-yl)-4,5-dihydro-1,3,4-thiadiazole-2-thiol |

TABLE 7

Hits below 65% residual activity for both replicates.

| MAC ID | R1 | R2 | Structure |
|---|---|---|---|
| MAC-0000090 | 14.81799 | 19.89361 | 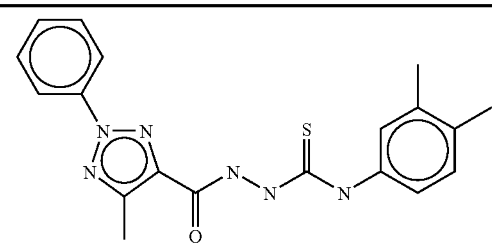 |

TABLE 7-continued

Hits below 65% residual activity for both replicates.

| MAC ID | R1 | R2 | Structure |
|---|---|---|---|
| MAC-0000232 | 63.45645 | 59.48434 | 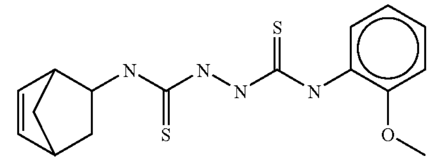 |
| MAC-0000311 | 32.35375 | 31.0296 | 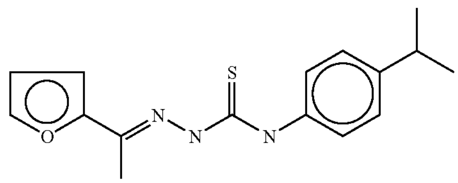 |
| MAC-0000398 | 49.52412 | 41.2882 | 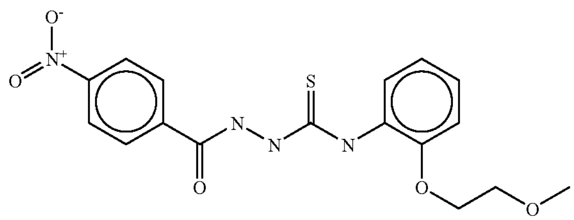 |
| MAC-0000510 | 23.24955 | 38.27487 | 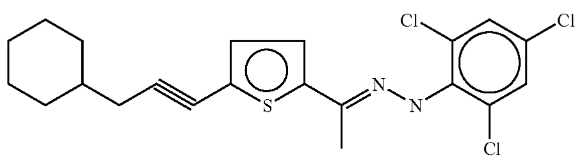 |
| MAC-0000552 | 23.40617 | 36.32593 | 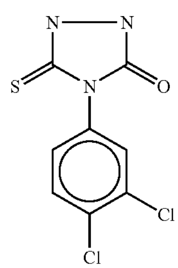 |
| MAC-0000685 | 25.50648 | 20.36264 | 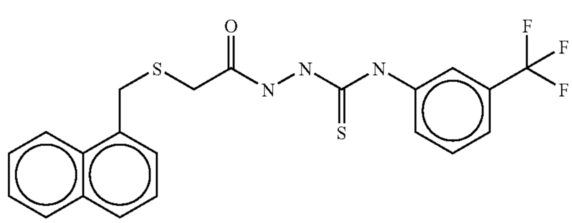 |
| MAC-0000924 | 59.37759 | 63.73389 | 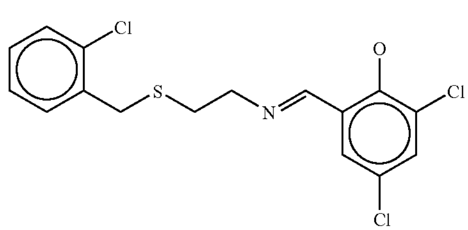 |

TABLE 7-continued

Hits below 65% residual activity for both replicates.

| MAC ID | R1 | R2 | Structure |
|---|---|---|---|
| MAC-0000917 | 56.3984 | 39.14712 | 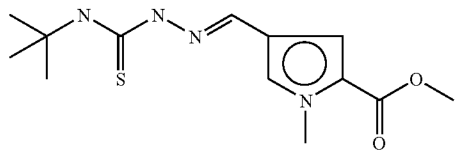 |
| MAC-0000993 | 59.12018 | 52.61719 | 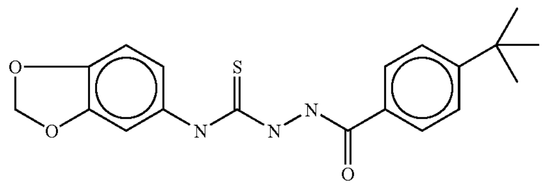 |

TABLE 8

| Structure | code | product_name |
|---|---|---|
| | BTB 03585 | N1-(3,4-dimethylphenyl)-2-[(5-methyl-2-phenyl-2H-1,2,3-triazol-4-yl)carbonyl]hydrazine-1-carbothioamide |
| | CD 01410 | N1-bicyclo[2.2.1]hept-5-en-2-yl-N2-(2-methoxyphenyl)hydrazine-1,2-dicarbothioamide |
| 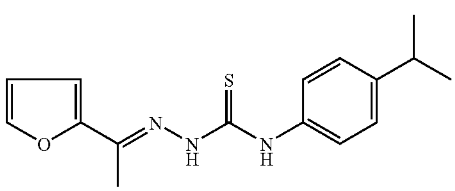 | DFP 00097 | N1-(4-isopropylphenyl)-2-[1-(2-furyl)ethylidene]hydrazine-1-carbothioamide |
| | BTB 03585 | N1-(3,4-dimethylphenyl)-2-[(5-methyl-2-phenyl-2H-1,2,3-triazol-4-yl)carbonyl]hydrazine-1-carbothioamide |
| | CD 01410 | N1-bicyclo[2.2.1]hept-5-en-2-yl-N2-(2-methoxyphenyl)hydrazine-1,2-dicarbothioamide |

TABLE 8-continued

| Structure | code | product_name |
|---|---|---|
| 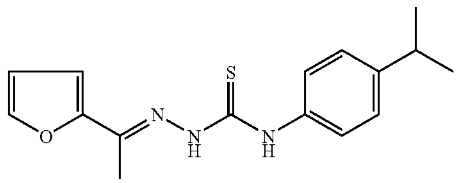 | DFP 00097 | N1-(4-isopropylphenyl)-2-[1-(2-furyl)ethylidene]hydrazine-1-carbothioamide |
| 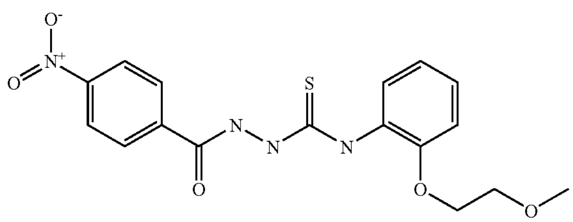 | GK 03686 | N-[2-(2-methoxyethoxy)phenyl]-2-(4-nitrobenzoyl)hydrazine-1-carbothioamide |
| 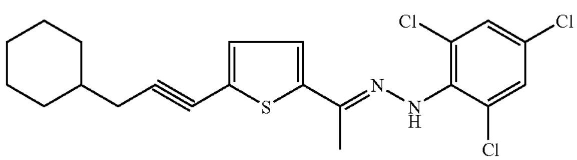 | KM 08967 | 1-[5-(3-cyclohexylprop-1-ynyl)-2-thienyl]ethan-1-one 1-(2,4,6-trichlorophenyl)hydrazone |
| 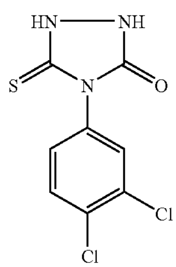 | NH 00306 | 4-(3,4-dichlorophenyl)-5-thioxo-1,2,4-triazolan-3-one |
| 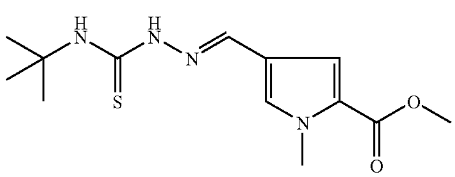 | SEW 06442 | methyl 4-{2-[(tert-butylamino)carbothioyl]carbohydrazonoyl}-1-methyl-1H-pyrrole-2-carboxylate |
| 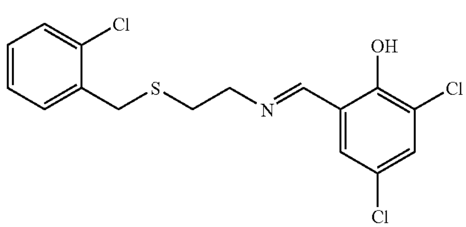 | SEW 06549 | 2,4-dichloro-6-[({2-[(2-chlorobenzyl)thio]ethyl}imino)methyl]phenol |
| 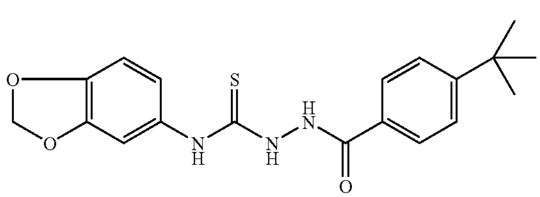 | TB 00026 | N-(1,3-benzodioxot-5-yl)-2-[4-(tert-butyl)benzoyl]hydrazine-1-carbothioamide |

TABLE 9

| Structure | Mol_ID | MOLENAME | plate | po |
|---|---|---|---|---|
| 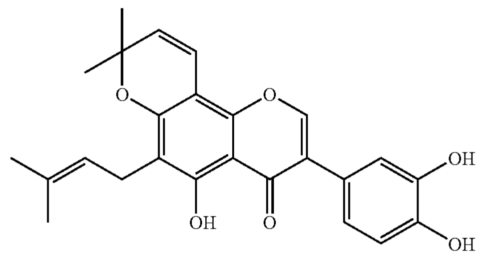 | 994 | POMIFERIN | 199163 | D05 |
| 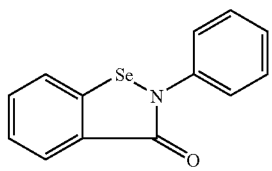 | 1002 | EBSELEN | 199163 | E03 |
| 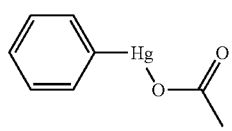 | 1003 | PHENYLMERCURIC ACETATE | 199163 | E04 |
| 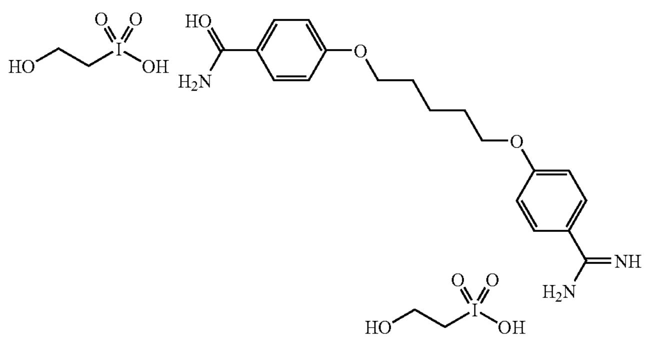 | 1006 | PENTAMIDINE ISETHIONATE | 199163 | E07 |
| 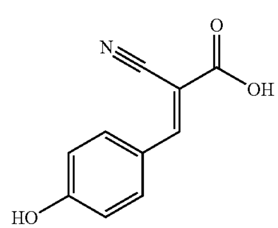 | 1012 | alpha-CYANO-4-HYDROXYCINNAMIC ACID | 199163 | F03 |
| 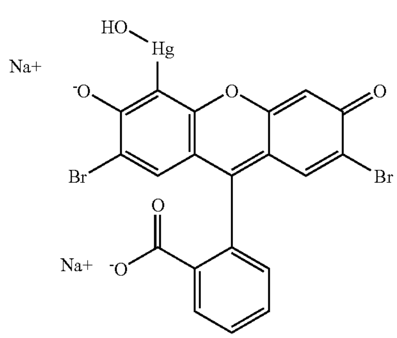 | 1013 | MERBROMIN | 199163 | F03 |

TABLE 9-continued

| Structure | Mol_ID | MOLENAME | plate | po |
|---|---|---|---|---|
| 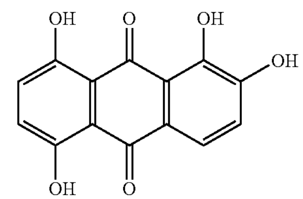 | 1017 | QUINALIZARIN | 199163 | F08 |
| 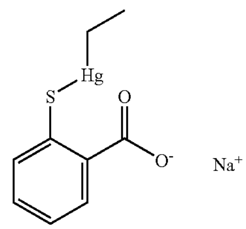 | 1022 | THIMEROSAL | 199163 | G03 |
| 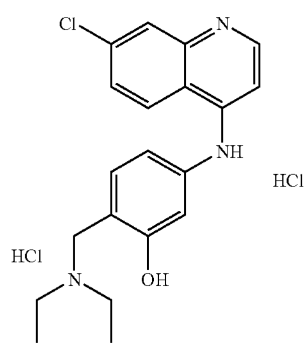 | 44 | AMODIAQUINE DIHYDROCHLORIDE | 199151 | E03 |
| 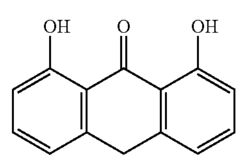 | 50 | ANTHRALIN | 199151 | E11 |
| 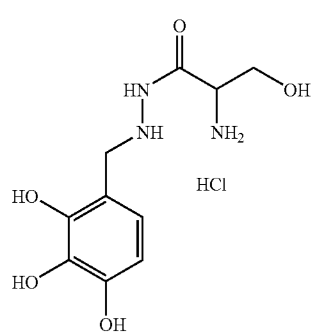 | 58 | BENSERAZIDE HYDROCHLORIDE | 199151 | F09 |

TABLE 9-continued

| Structure | Mol_ID | MOLENAME | plate | po |
|---|---|---|---|---|
| 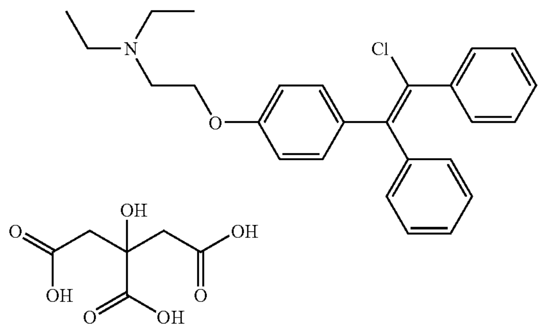 | 109 | CLOMIPHENE CITRATE | 199152 | C10 |
| 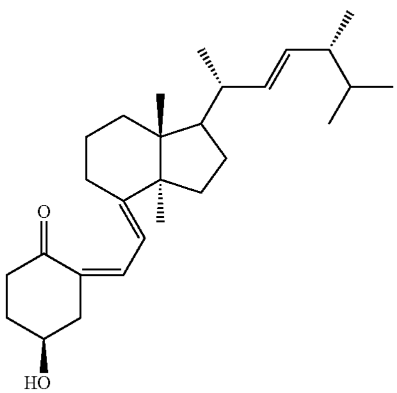 | 163 | ERGOCALCIFEROL | 199153 | A04 |
| 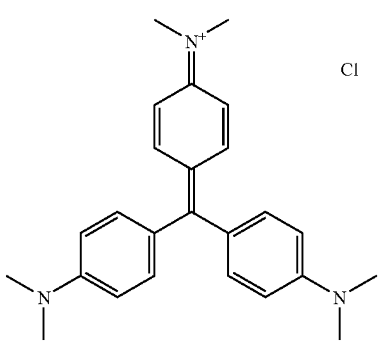 | 187 | GENTIAN VIOLET | 199153 | C08 |
| 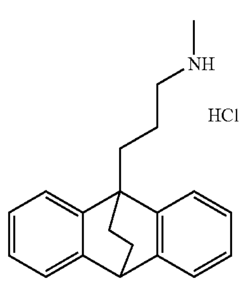 | 229 | MAPROTILINE HYDROCHLORIDE | 199153 | G10 |
| 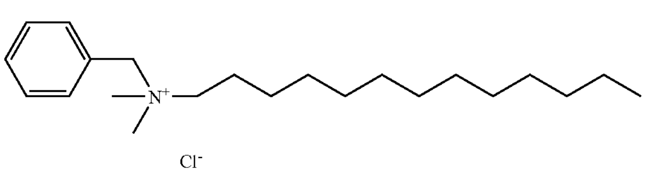 | 279 | BENZALKONIUM CHLORIDE | 199154 | D10 |

TABLE 9-continued

| Structure | Mol_ID | MOLENAME | plate | po |
|---|---|---|---|---|
| 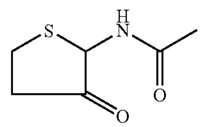 | 337 | CITIOLONE | 199155 | B08 |
| 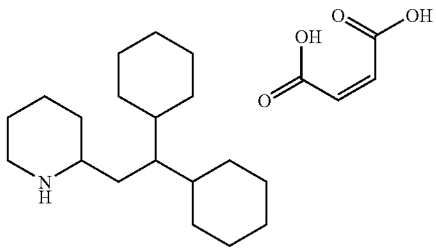 | 352 | PERHEXILINE MALEATE | 199155 | D03 |
| 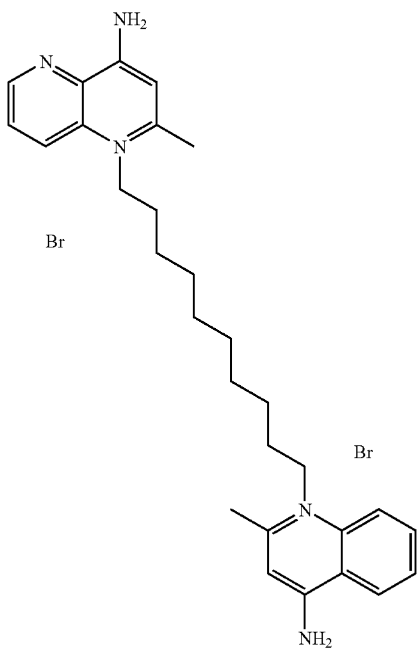 | 353 | DEQUALINIUM CHLORIDE | 199155 | D04 |
| 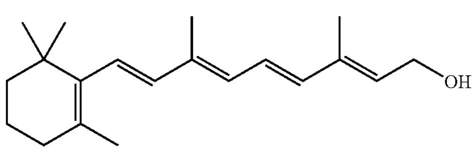 | 407 | RETINOL | 199156 | A08 |
| 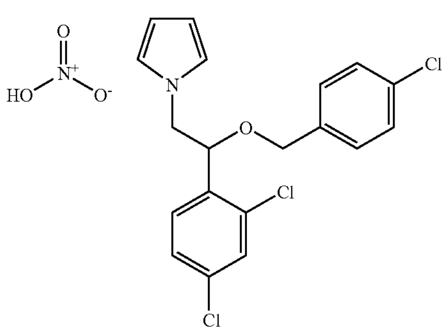 | 417 | ECONAZOLE NITRATE | 199156 | B06 |

TABLE 9-continued

| Structure | Mol_ID | MOLENAME | plate | po |
|---|---|---|---|---|
| 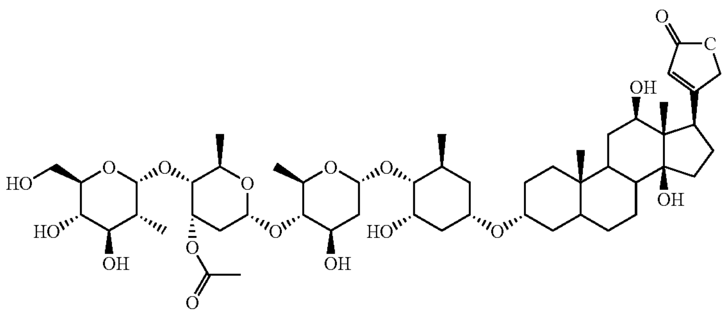 | 429 | LANATOSIDE C | 199156 | C10 |
| 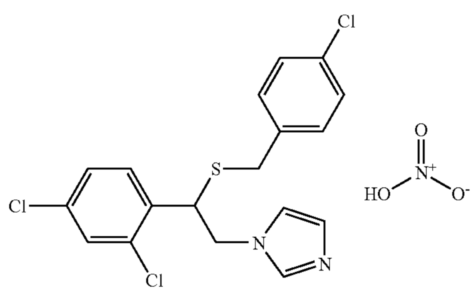 | 448 | SULCONAZOLE NITRATE | 199156 | E09 |
| 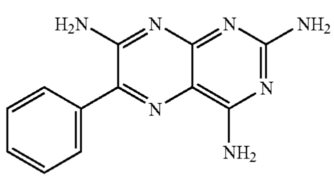 | 497 | TRIAMTERENE | 199157 | B08 |
| 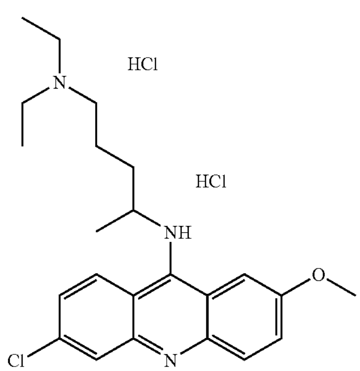 | 593 | QUINACRINE HYDROCHLORIDE | 199158 | D04 |
| 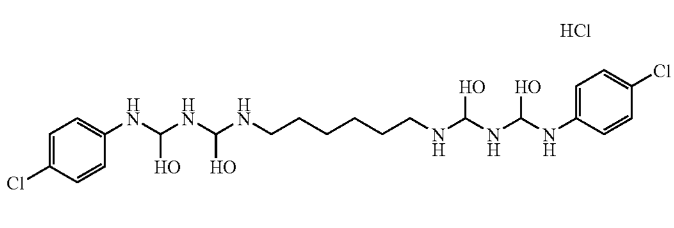 | 651 | CHLORHEXIDINE | 199159 | B02 |

TABLE 9-continued

| Structure | Mol_ID | MOLENAME | plate | po |
|---|---|---|---|---|
| 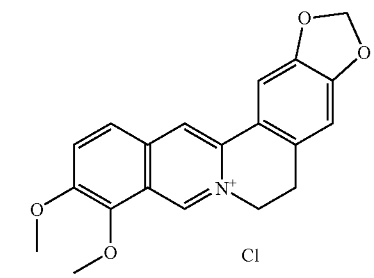 | 689 | BERBERINE CHLORIDE | 199159 | E10 |
| 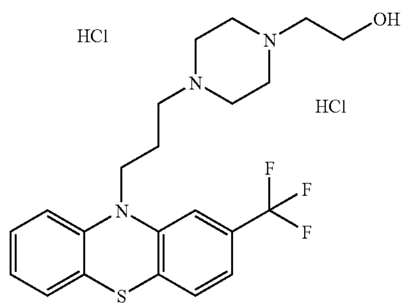 | 708 | FLUFENAZINE HYDROCHLORIDE | 199159 | G09 |
| 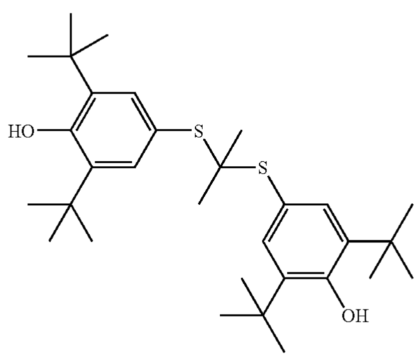 | 732 | PROBUCOL | 199160 | B03 |
| 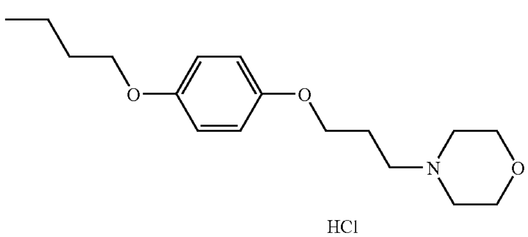 | 776 | PRAMOXINE HYDROCHLORIDE | 199160 | F07 |
| 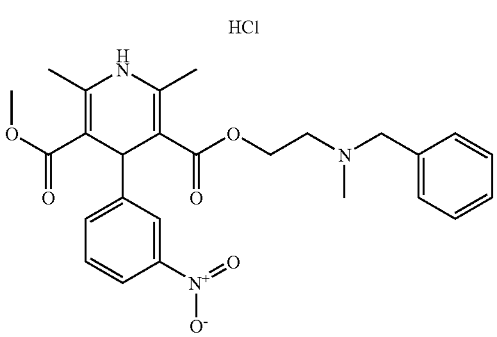 | 810 | NICARDIPINE HYDROCHLORIDE | 199161 | A11 |

TABLE 9-continued

| Structure | Mol_ID | MOLENAME | plate | po |
|---|---|---|---|---|
| 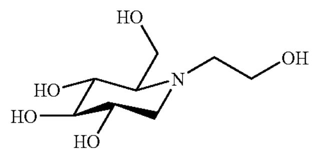 | 845 | MIGLITOL | 199161 | E06 |
| 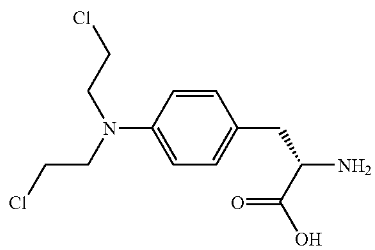 | 881 | MELPHALAN | 199162 | A02 |
| 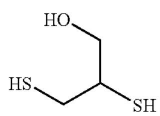 | 886 | DIMERCAPTOPROPANOL | 199162 | A07 |
| 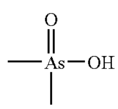 | 902 | CACODYLIC ACID | 199162 | C03 |
| 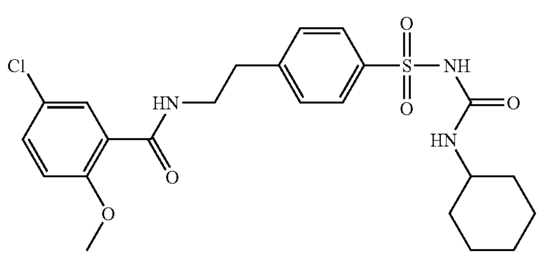 | 923 | GLYBURIDE | 199162 | E04 |
| 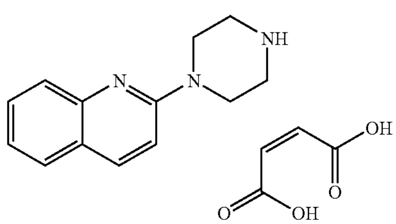 | 927 | QUIPAZINE MALEATE | | |
| 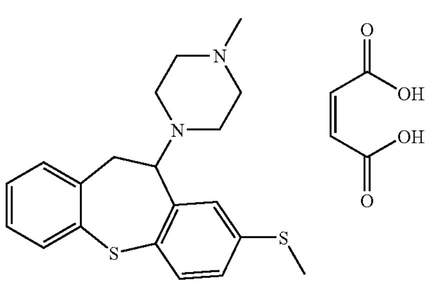 | 945 | METHIOTHEPIN MALEATE | | |

TABLE 9-continued

| Structure | Mol_ID | MOLENAME | plate | po |
|---|---|---|---|---|
| 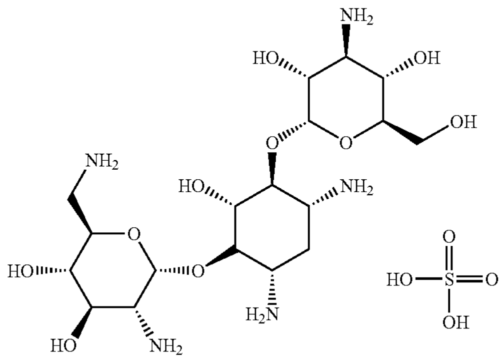 | 977 | BECANAMYCIN SULFATE | | |
| 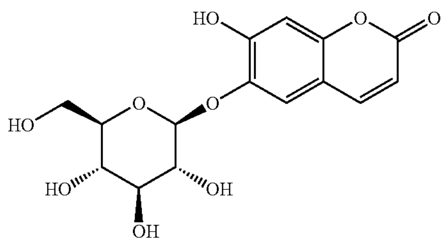 | 989 | AESCULIN | | |

The invention claimed is

1. method for treating, in a subject, a disease associated with reduced activity of hexosaminidase, comprising administering to the subject an effective amount of a compound selected from the group consisting of pyrimethamine and probucol.

2. The method of claim 1 wherein the disease is selected from the group consisting of Tay Sachs disease and Sandhoff disease.

3. The method of claim 2 wherein the Tay Sachs disease is adult onset Tay Sachs disease and the compound administered to the subject is pyrimethamine.

* * * * *

UNITED STATES PATENT AND TRADEMARK OFFICE
CERTIFICATE OF CORRECTION

PATENT NO.         : 7,488,721 B2
APPLICATION NO.    : 11/129274
DATED              : February 10, 2009
INVENTOR(S)        : Mahuran et al.

It is certified that error appears in the above-identified patent and that said Letters Patent is hereby corrected as shown below:

On Title Page:
Item 75, Inventors: Please delete "Eric Brown, Oakville (CA)"

At columns 13-14, compound BTB 14232:    Replace the structure

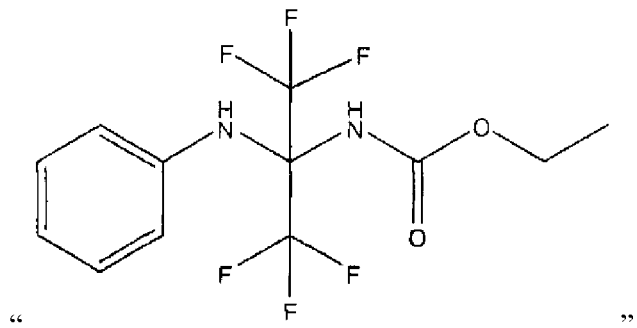

"                                                                                    "

With the structure

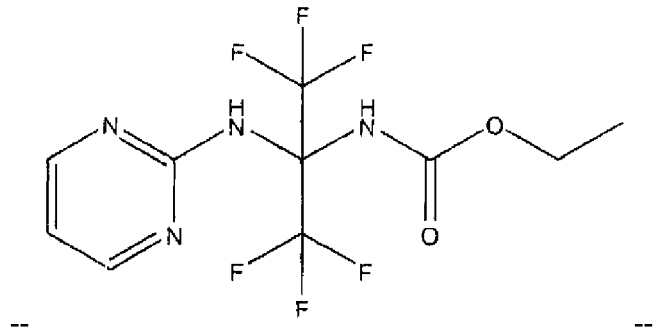

--                                                                                  --

At columns 15-16, compound HTS 07376:    Replace the structure

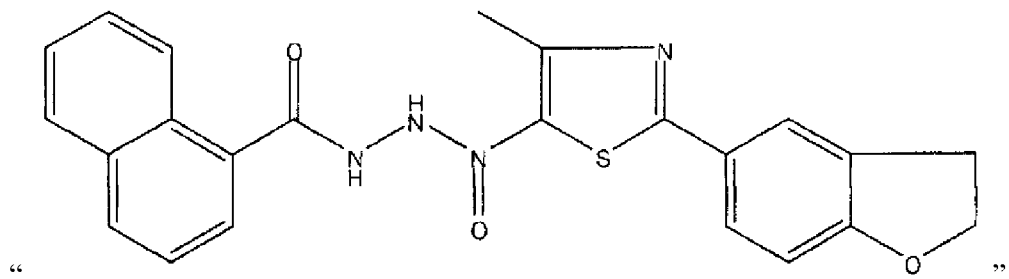

"                                                                                    "

UNITED STATES PATENT AND TRADEMARK OFFICE
CERTIFICATE OF CORRECTION

PATENT NO.        : 7,488,721 B2
APPLICATION NO. : 11/129274
DATED             : February 10, 2009
INVENTOR(S)       : Mahuran et al.

It is certified that error appears in the above-identified patent and that said Letters Patent is hereby corrected as shown below:

With the structure

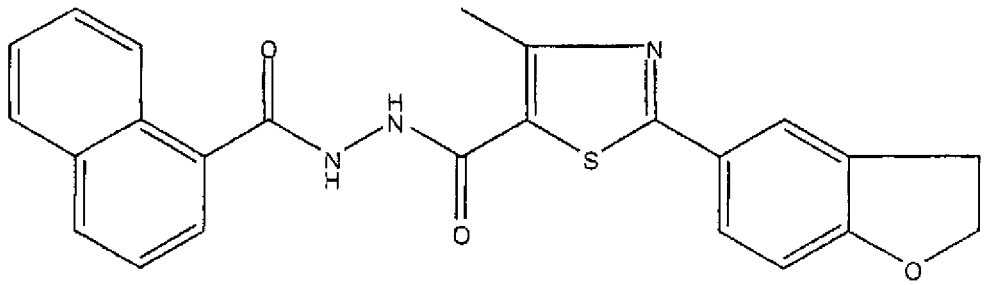

At columns 15-16, compound JFD 02998:    Replace the structure

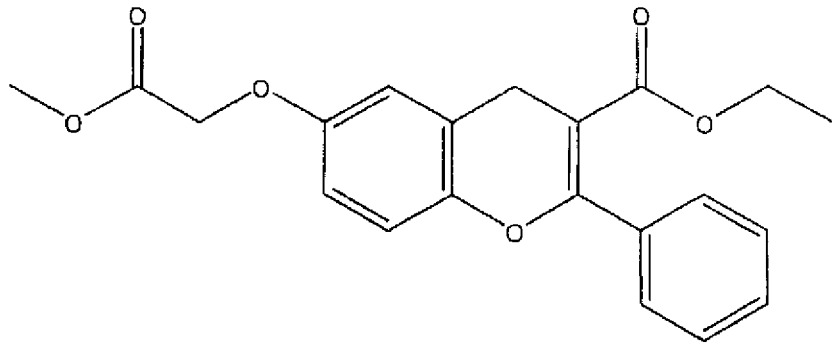

"                                                                                       "

With the structure

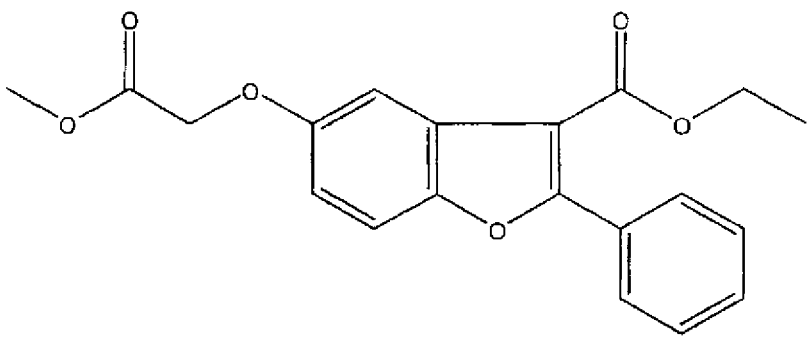

UNITED STATES PATENT AND TRADEMARK OFFICE
CERTIFICATE OF CORRECTION

PATENT NO. : 7,488,721 B2  
APPLICATION NO. : 11/129274  
DATED : February 10, 2009  
INVENTOR(S) : Mahuran et al.

It is certified that error appears in the above-identified patent and that said Letters Patent is hereby corrected as shown below:

At columns 17-18, compound KM 06825:     Replace the structure

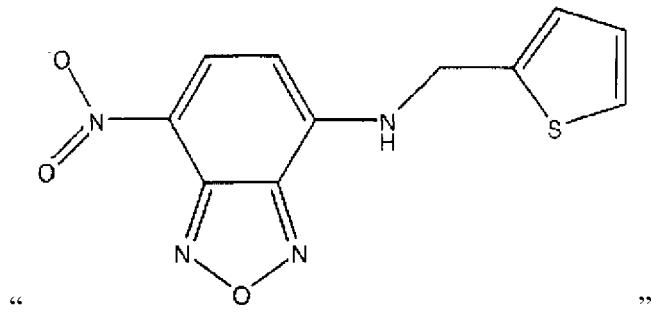

"                                                                          "

With the structure

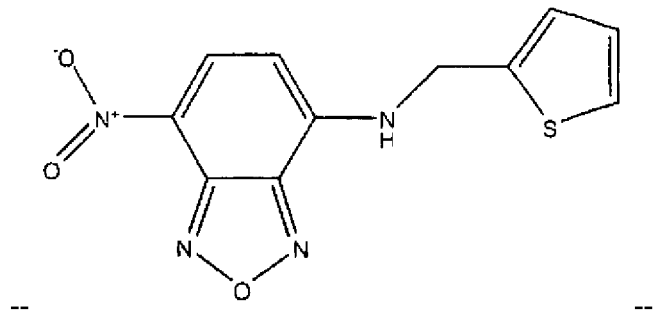

--                                                                           --

At columns 17-18, compound KM 08092:     Replace the structure

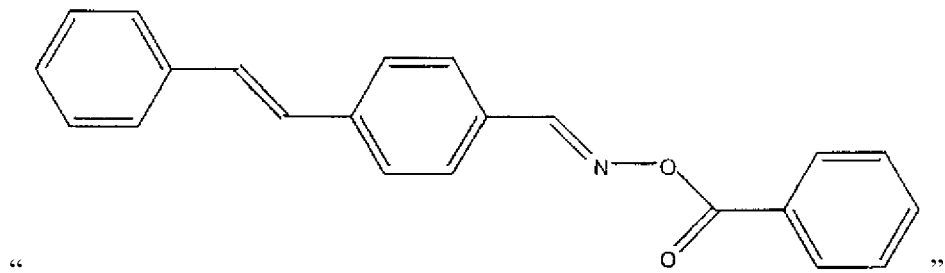

"                                                                          "

UNITED STATES PATENT AND TRADEMARK OFFICE
CERTIFICATE OF CORRECTION

PATENT NO.       : 7,488,721 B2
APPLICATION NO.  : 11/129274
DATED            : February 10, 2009
INVENTOR(S)      : Mahuran et al.

It is certified that error appears in the above-identified patent and that said Letters Patent is hereby corrected as shown below:

With the structure

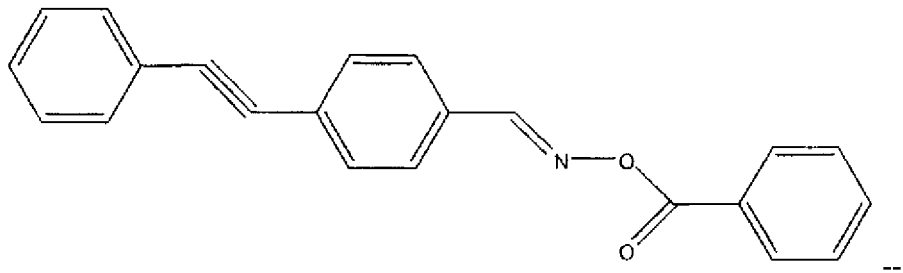

-- --

At columns 29-30, compound GK 03686:    Replace the structure

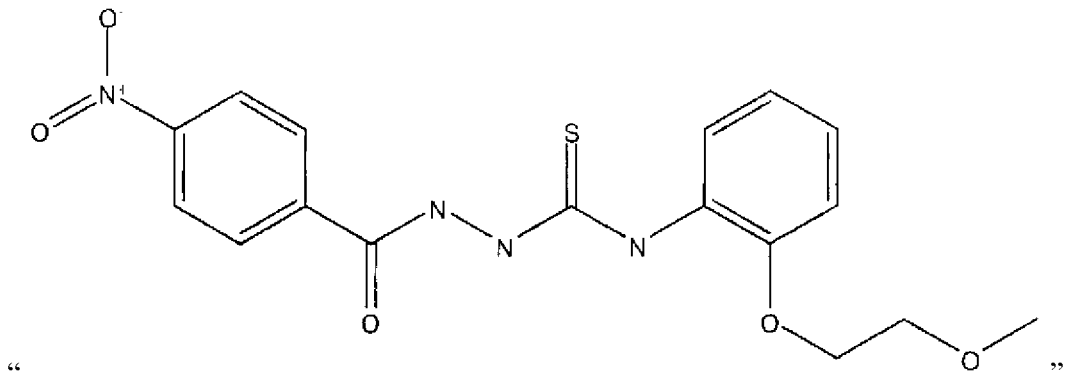

"                                                                                "

With the structure

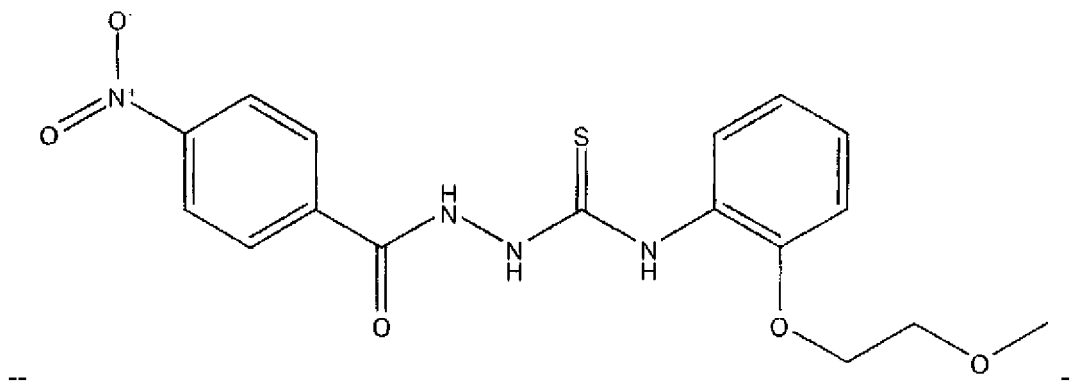

-- --

UNITED STATES PATENT AND TRADEMARK OFFICE
CERTIFICATE OF CORRECTION

PATENT NO. : 7,488,721 B2
APPLICATION NO. : 11/129274
DATED : February 10, 2009
INVENTOR(S) : Mahuran et al.

It is certified that error appears in the above-identified patent and that said Letters Patent is hereby corrected as shown below:

At columns 31-32, compound 1006:     Replace the structure

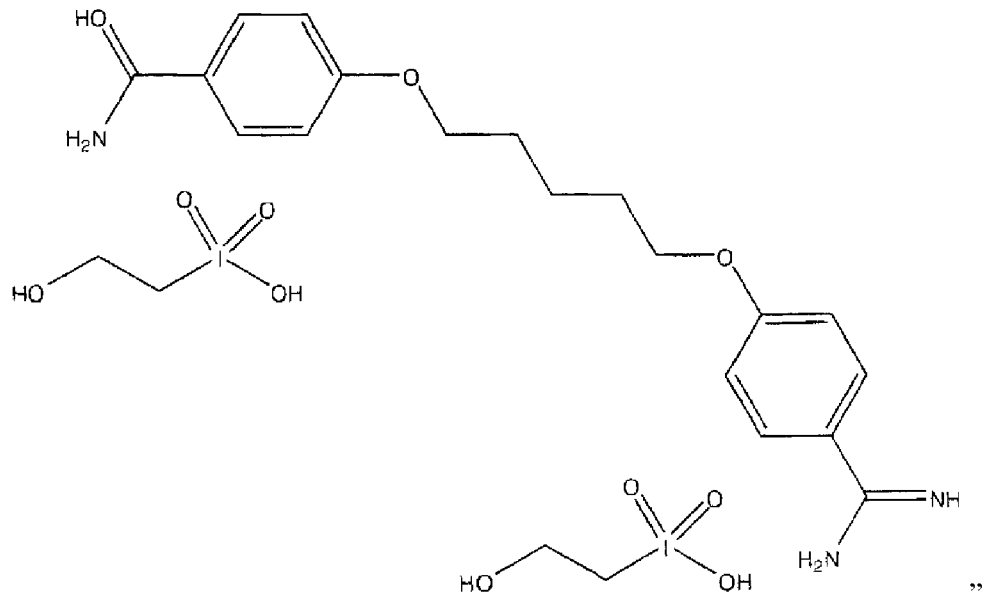

"                                                                                    "

With the structure

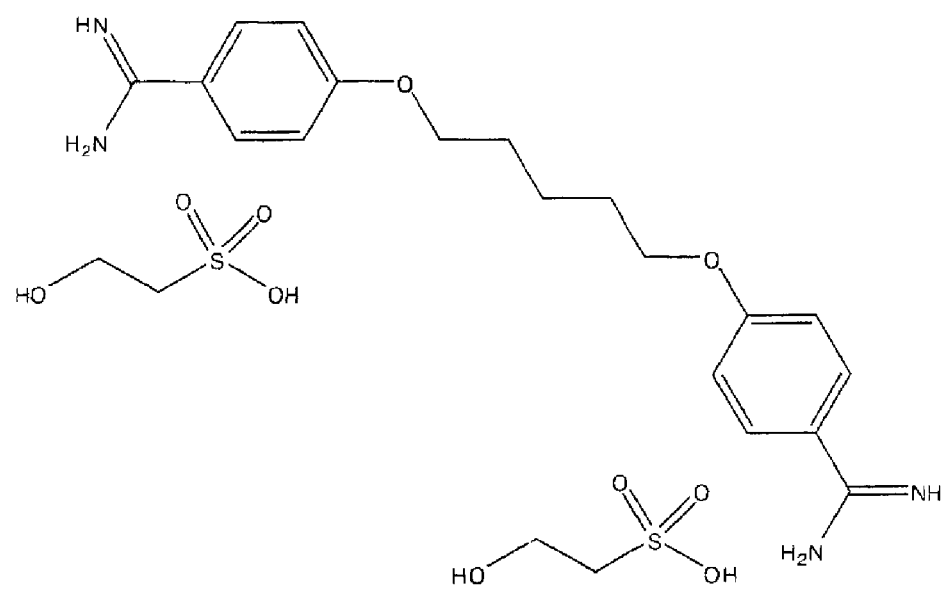

UNITED STATES PATENT AND TRADEMARK OFFICE
CERTIFICATE OF CORRECTION

PATENT NO.         : 7,488,721 B2
APPLICATION NO.    : 11/129274
DATED              : February 10, 2009
INVENTOR(S)        : Mahuran et al.

It is certified that error appears in the above-identified patent and that said Letters Patent is hereby corrected as shown below:

At columns 35-36, compound 163:       Replace the structure

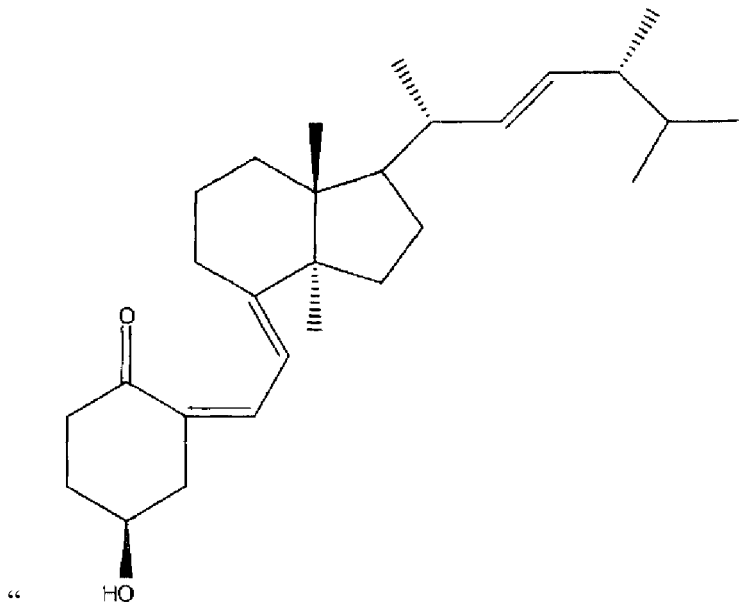

"                                                                    "

With the structure

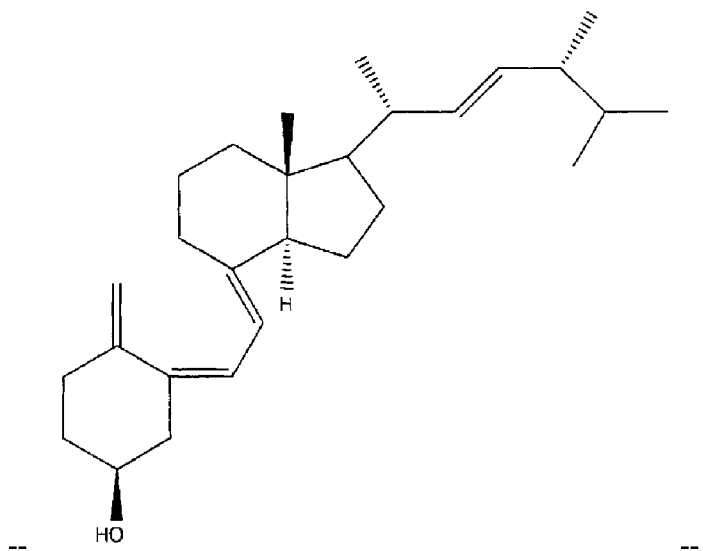

--                                                                   --

UNITED STATES PATENT AND TRADEMARK OFFICE
CERTIFICATE OF CORRECTION

PATENT NO.        : 7,488,721 B2
APPLICATION NO.   : 11/129274
DATED             : February 10, 2009
INVENTOR(S)       : Mahuran et al.

It is certified that error appears in the above-identified patent and that said Letters Patent is hereby corrected as shown below:

At columns 35-36, compound 187:     Replace "Cl" with --Cl⁻--

At columns 37-38, compound 353:     Replace the structure

"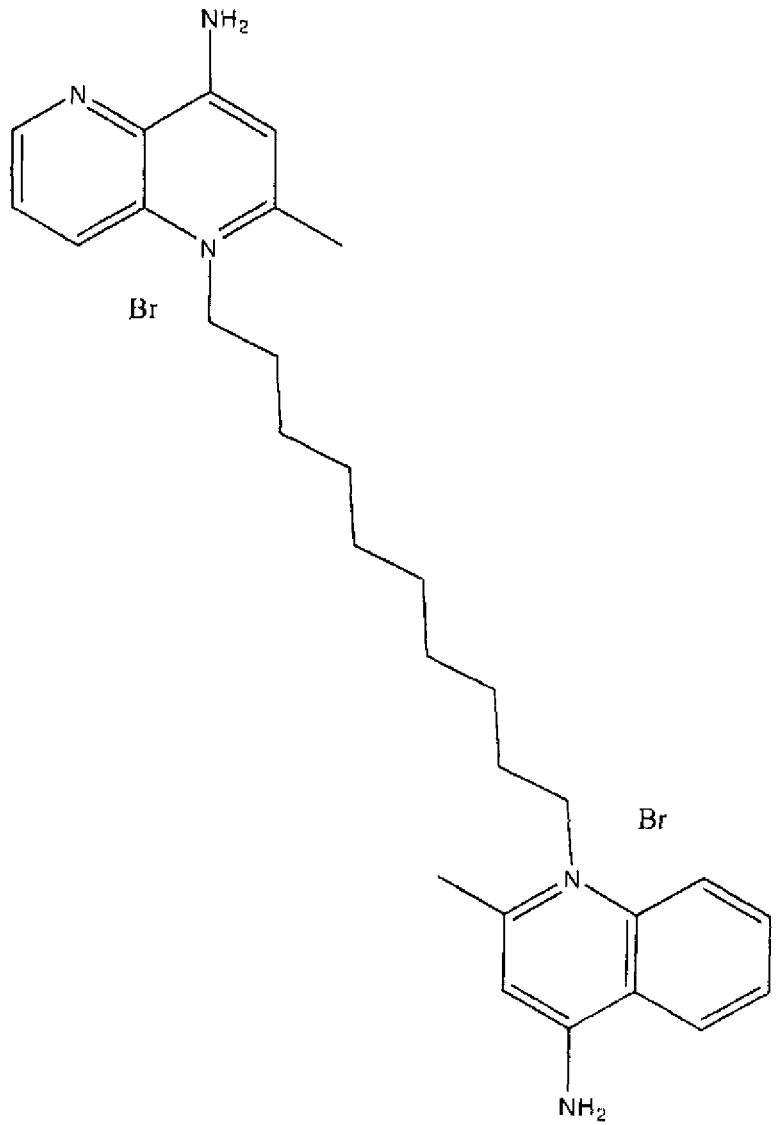"

UNITED STATES PATENT AND TRADEMARK OFFICE
CERTIFICATE OF CORRECTION

PATENT NO.      : 7,488,721 B2
APPLICATION NO. : 11/129274
DATED           : February 10, 2009
INVENTOR(S)     : Mahuran et al.

It is certified that error appears in the above-identified patent and that said Letters Patent is hereby corrected as shown below:

With the structure

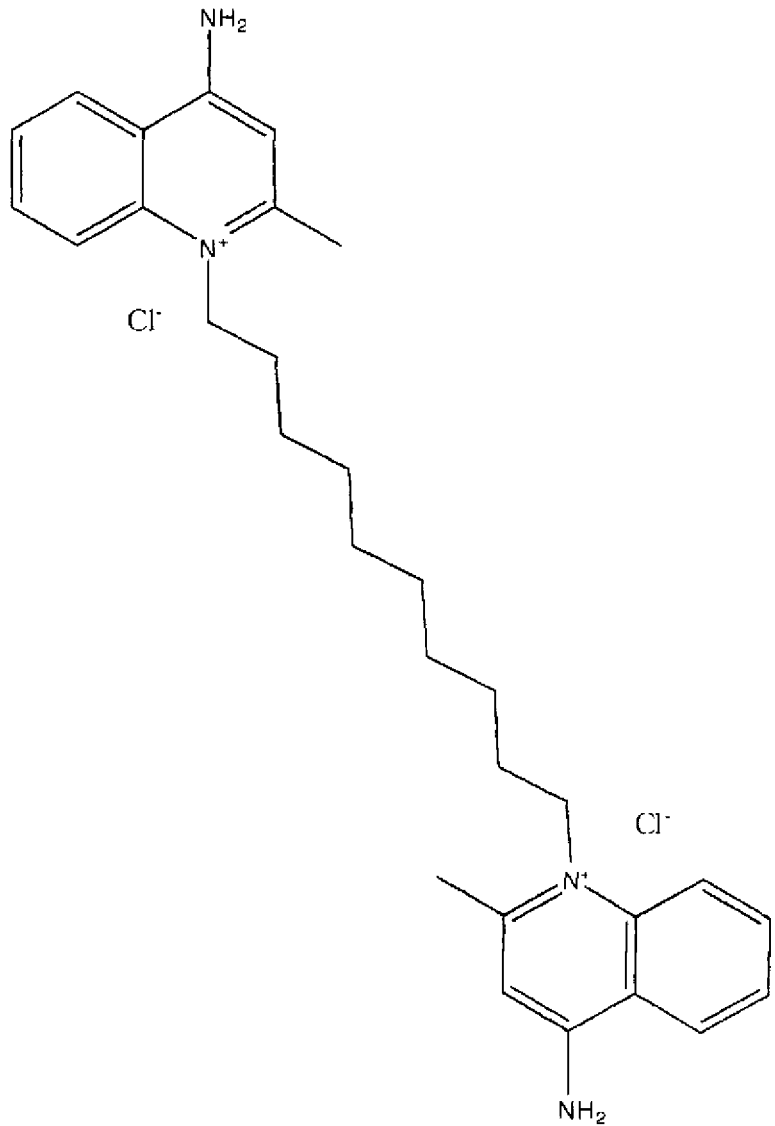

UNITED STATES PATENT AND TRADEMARK OFFICE
CERTIFICATE OF CORRECTION

PATENT NO. : 7,488,721 B2
APPLICATION NO. : 11/129274
DATED : February 10, 2009
INVENTOR(S) : Mahuran et al.

It is certified that error appears in the above-identified patent and that said Letters Patent is hereby corrected as shown below:

At columns 37-38, compound 417:   Replace the structure

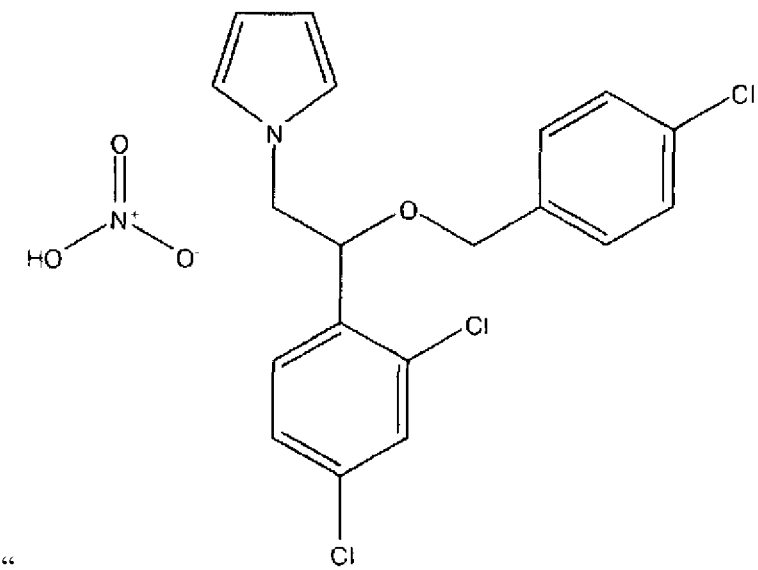

"

With the structure

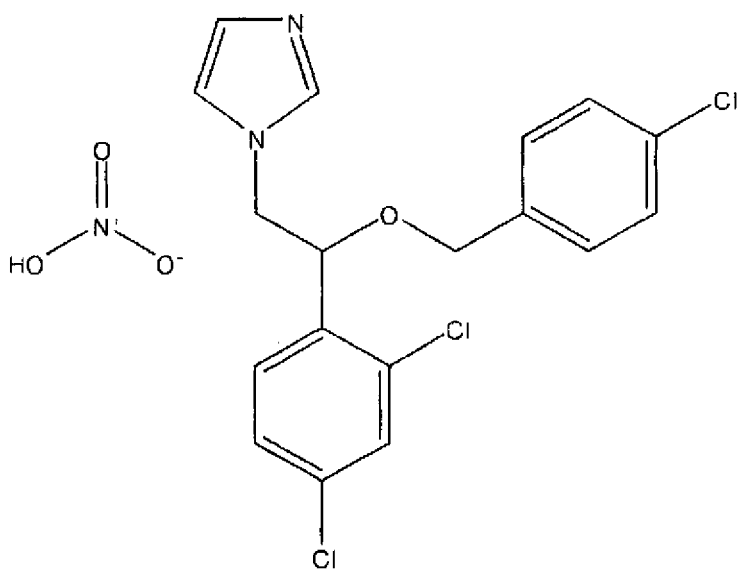

--

UNITED STATES PATENT AND TRADEMARK OFFICE
CERTIFICATE OF CORRECTION

PATENT NO. : 7,488,721 B2
APPLICATION NO. : 11/129274
DATED : February 10, 2009
INVENTOR(S) : Mahuran et al.

It is certified that error appears in the above-identified patent and that said Letters Patent is hereby corrected as shown below:

At columns 39-40, compound 429:        Replace the structure

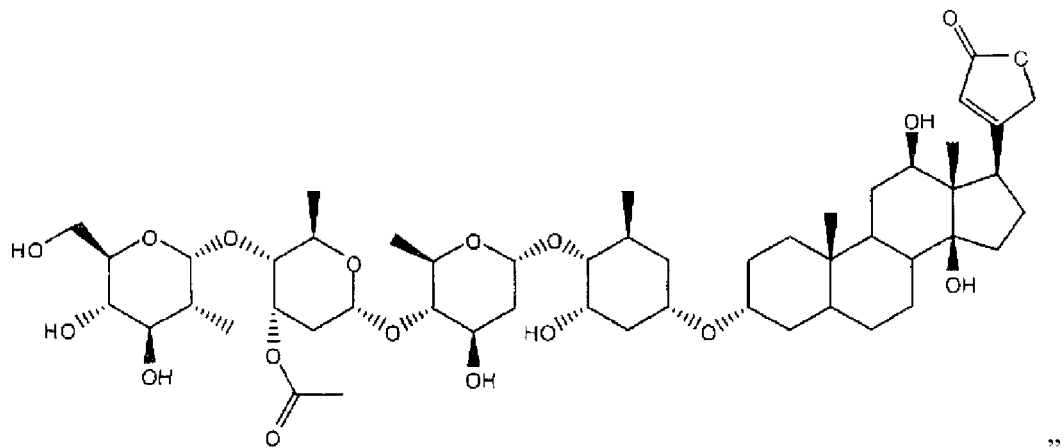

"                                                                                              "

With the structure

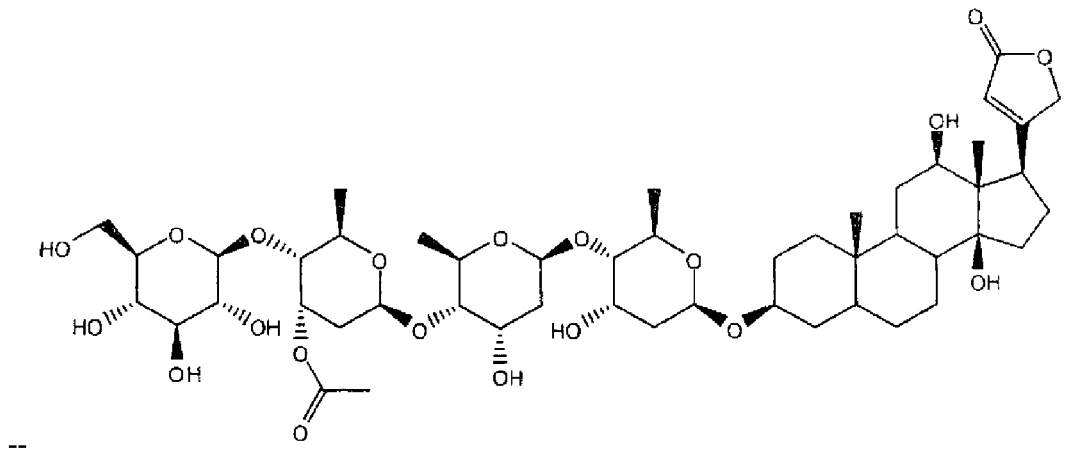

--                                                                                              --

UNITED STATES PATENT AND TRADEMARK OFFICE
CERTIFICATE OF CORRECTION

PATENT NO. : 7,488,721 B2
APPLICATION NO. : 11/129274
DATED : February 10, 2009
INVENTOR(S) : Mahuran et al.

It is certified that error appears in the above-identified patent and that said Letters Patent is hereby corrected as shown below:

At columns 39-40, compound 651:   Replace the structure

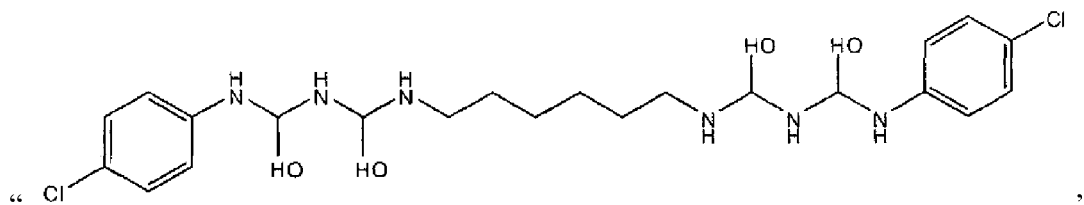

With the structure

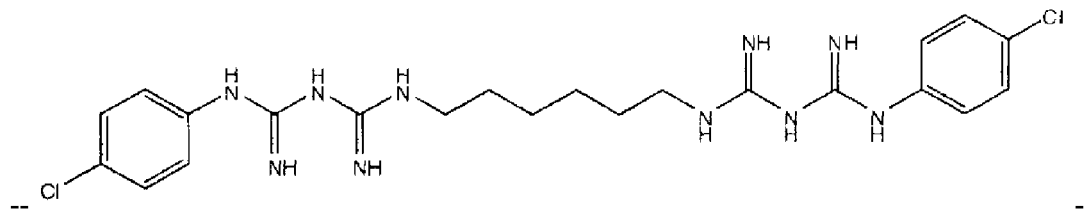

At columns 41-42, compound 689:   Replace "Cl" with --Cl⁻--

At column 45, line 35:   Insert --A-- before "method"

Signed and Sealed this

Third Day of November, 2009

David J. Kappos
*Director of the United States Patent and Trademark Office*

UNITED STATES PATENT AND TRADEMARK OFFICE
CERTIFICATE OF CORRECTION

PATENT NO.        : 7,488,721 B2
APPLICATION NO.   : 11/129274
DATED             : February 10, 2009
INVENTOR(S)       : Mahuran et al.

It is certified that error appears in the above-identified patent and that said Letters Patent is hereby corrected as shown below:

On Title Page:

Item 73, Assignees: Please delete "McMaster University, Hamilton, Ontario (CA)"

Signed and Sealed this

Thirtieth Day of March, 2010

David J. Kappos
*Director of the United States Patent and Trademark Office*